(12) United States Patent
Olsson

(10) Patent No.: US 12,371,513 B2
(45) Date of Patent: Jul. 29, 2025

(54) POST-CROSSLINKING PARTIAL DEGRADATION OF AMIDE CROSSLINKED HYDROGELS

(71) Applicant: Galderma Holding SA, La Tour-de-Peliz (CH)

(72) Inventor: Johan Olsson, Bromma (SE)

(73) Assignee: Galderma Holding SA, Zug (CH)

( * ) Notice: Subject to any disclaimer, the term of this patent is extended or adjusted under 35 U.S.C. 154(b) by 943 days.

(21) Appl. No.: 17/334,373

(22) Filed: May 28, 2021

(65) Prior Publication Data

US 2021/0284759 A1    Sep. 16, 2021

Related U.S. Application Data

(63) Continuation of application No. PCT/IB2019/060199, filed on Nov. 26, 2019.

(30) Foreign Application Priority Data

Nov. 29, 2018 (EP) .................................... 18209081

(51) Int. Cl.
| | |
|---|---|
| C08B 37/08 | (2006.01) |
| A61K 8/04 | (2006.01) |
| A61K 8/73 | (2006.01) |
| A61Q 19/00 | (2006.01) |
| C08K 5/00 | (2006.01) |
| C08K 5/1545 | (2006.01) |
| C08L 5/08 | (2006.01) |

(52) U.S. Cl.
CPC .......... *C08B 37/0072* (2013.01); *A61K 8/042* (2013.01); *A61K 8/735* (2013.01); *A61Q 19/00* (2013.01); *C08K 5/0025* (2013.01); *C08K 5/1545* (2013.01); *C08L 5/08* (2013.01); *A61K 2800/10* (2013.01)

(58) Field of Classification Search
CPC ... C08B 37/0072; C08L 5/08; A61K 2800/10; A61K 8/042; A61K 8/735
See application file for complete search history.

(56) References Cited

U.S. PATENT DOCUMENTS

| | | | |
|---|---|---|---|
| 6,703,444 B2 | 3/2004 | Zhao et al. | |
| 6,831,172 B1 | 12/2004 | Barbucci et al. | |
| 8,858,999 B2 | 10/2014 | Giammona et al. | |
| 8,887,243 B2 | 11/2014 | Thomson et al. | |
| 11,198,765 B2 * | 12/2021 | Olsson | ................ C08B 37/0072 |
| 2007/0066816 A1 | 3/2007 | Tsai et al. | |
| 2019/0010113 A1 * | 1/2019 | Jing Jing | .................. C08L 5/08 |
| 2019/0016830 A1 | 1/2019 | Olsson et al. | |
| 2019/0023812 A1 | 1/2019 | Mojarradi et al. | |
| 2019/0023855 A1 | 1/2019 | Olsson et al. | |

FOREIGN PATENT DOCUMENTS

| | | |
|---|---|---|
| EP | 3 187 510 A1 | 7/2017 |
| EP | 3 252 081 A1 | 12/2017 |
| WO | WO-2017/114861 | 7/2017 |
| WO | WO-2017/114864 | 7/2017 |
| WO | WO-2017/114865 | 7/2017 |
| WO | WO-2017/114867 A1 | 7/2017 |
| WO | WO-2019/002368 A1 | 1/2019 |
| WO | WO-2019/002370 A1 | 1/2019 |

OTHER PUBLICATIONS

International Search Report and Written Opinion for Appl. Ser. No. PCT/IB2019/060199 dated Feb. 4, 2020 (14 pages).
Kurita et al., "Synthetic Carbohydrate Polymers Containing Trehalose Residues in the Main Chain: Preparation and Characteristic Properties", Macromolecules 1994, vol. 27, pp. 7544-7549.

* cited by examiner

*Primary Examiner* — Pancham Bakshi
(74) *Attorney, Agent, or Firm* — Sunit Talapatra; Foley & Lardner LLP

(57) ABSTRACT

The present disclosure provides a method of preparing a hydrogel product comprising crosslinked glycosaminoglycan molecules at a concentration $C_{final}$ (mg/mL). The method comprising the steps of: a) crosslinking a glycosaminoglycan having a molecular weight of above 700 kDa in conditions so as to provide a glycosaminoglycan hydrogel crosslinked by amide bonds and having a $C_{min}$ (mg/mL) that is above $C_{final}/2$, wherein $C_{min}$ is the concentration of gel-form glycosaminoglycan in the gel when fully swollen in physiological buffer; b) subjecting the hydrogel from step a) to post-crosslinking degradation of the glycosaminoglycan backbone, thereby reducing the $C_{min}$ of the hydrogel to a value that is below $C_{final}/2$; and c) formulating the partially degraded hydrogel obtained from step b) to form an injectable hydrogel composition having a concentration of glycosaminoglycan molecules of $C_{final}$ (mg/mL).

17 Claims, 1 Drawing Sheet

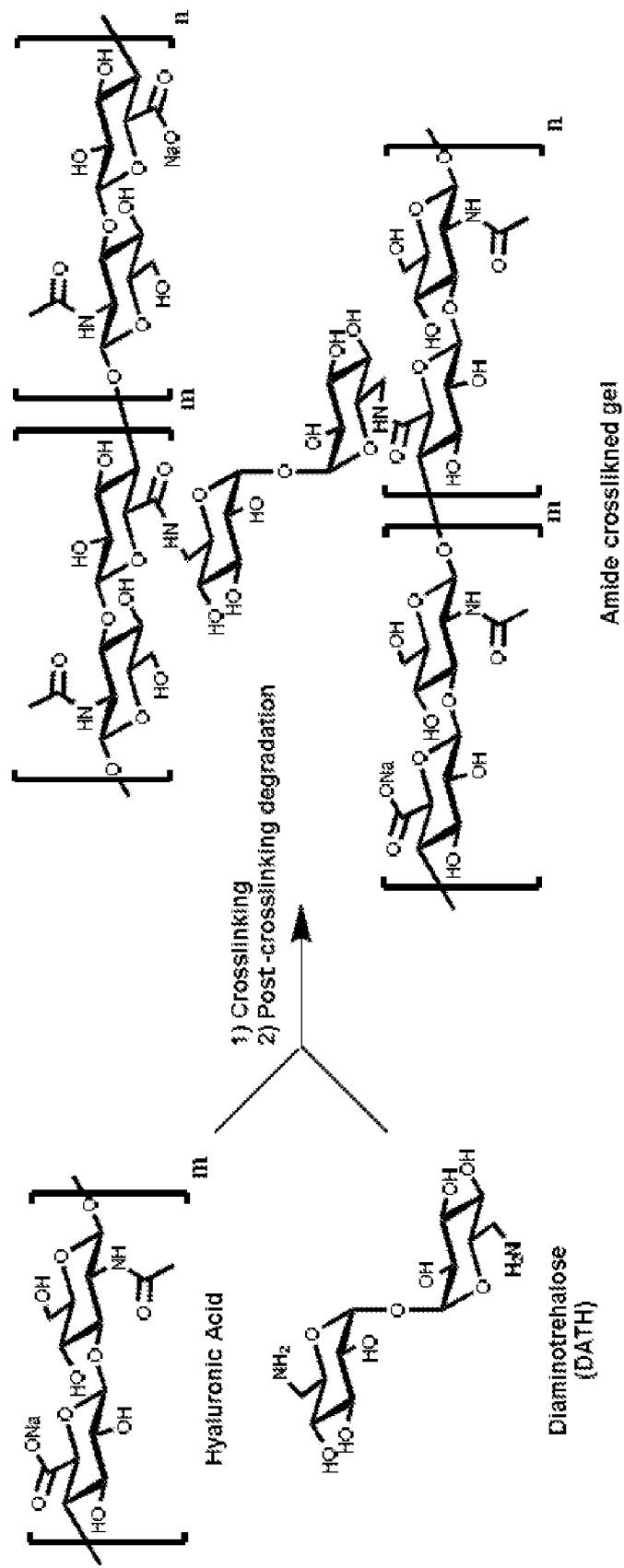

POST-CROSSLINKING PARTIAL DEGRADATION OF AMIDE CROSSLINKED HYDROGELS

CROSS-REFERENCE TO RELATED APPLICATIONS

The present application is a continuation of and claims the benefit of priority to International Application No. PCT/IB2019/060199 filed Nov. 26, 2019, which claims the benefit of priority to EP Application No. EP18209081, filed Nov. 29, 2018, the entire contents of each are incorporated herein by reference.

FIELD

The present disclosure relates to the field of high molecular weight esthetic compositions such as hydrogels containing crosslinked polysaccharides, and the use of such hydrogels in medical and/or cosmetic applications such as implants for subcutaneous or intradermal injection, which may be used in humans in reparative or plastic surgery and in esthetic dermatology. More specifically, the present disclosure is concerned with hydrogels comprising crosslinked high molecular weight glycosaminoglycans (GAGs), particularly crosslinked hyaluronic acid, chondroitin, or chondroitin sulfate The present disclosure relates to the field of hydrogels containing crosslinked polysaccharides and the use of such hydrogels in medical and/or cosmetic applications. More specifically, the present disclosure deals with amide crosslinked hyaluronic acid hydrogels.

BACKGROUND

One of the most widely used biocompatible polymers for medical use is hyaluronic acid (HA). It is a naturally occurring polysaccharide belonging to the group of glycosaminoglycans (GAGs). Hyaluronic acid and the other GAGs are negatively charged heteropolysaccharide chains which have a capacity to absorb large amounts of water. Hyaluronic acid and products derived from hyaluronic acid are widely used in the biomedical and cosmetic fields, for instance during viscosurgery and as a dermal filler.

Since hyaluronic acid is present with identical chemical structure except for its molecular mass in most living organisms, it gives a minimum of reactions and allows for advanced medical uses. Crosslinking and/or other modifications of the hyaluronic acid molecule is necessary to improve its duration in vivo.

Water-absorbing gels, or hydrogels, are widely used in the biomedical field. They are generally prepared by chemical crosslinking of polymers to infinite networks. While native hyaluronic acid absorb water until they are completely dissolved, crosslinked hyaluronic acid gels typically absorb a certain amount of water until they are saturated, i.e. they have a finite liquid retention capacity, or swelling degree A common route for crosslinking hyaluronic acid is using a diglycidyl ether, e.g. 1,4-butanediol diglycidyl ether (BDDE). As an alternative, amide coupling using a di- or multiamine functional crosslinker together with a coupling agent is an attractive route for preparing crosslinked hyaluronic acid molecules useful for hydrogel products. For example, the use of 4-(4,6-Dimethoxy-1,3,5-triazin-2-yl)-4-methylmorpholinium chloride (DMTMM) for activation of carboxylate and subsequent condensation with a diamino structure, e.g. diaminotrehalose (DATH) has shown to be an efficient method to produce hydrogels composed of crosslinked hyaluronic acid with minor degradation of the biopolymer. There is however a need in the art for improved methods for producing hydrogels of amide crosslinked glycosaminoglycans.

SUMMARY OF THE DISCLOSURE

It is an object of the present disclosure to provide a crosslinked glycosaminoglycan product, such as hyaluronic acid product, suitable for use as a dermal filler.

It is a further object of the present disclosure to provide a crosslinked glycosaminoglycan product, such as hyaluronic acid product, from high molecular weight (HMW) glycosaminoglycan using amide crosslinking.

It is a further object of the present disclosure to provide a crosslinked hyaluronic acid product from HMW hyaluronic acid using DATH/DMTMM chemistry that can be formulated to suitable hyaluronic acid concentrations for dermatological use ($C_{final}$ of 10-30 mg/mL).

For these and other objects that is evident from this disclosure, the present disclosure provides according to a first aspect thereof, a method of preparing a hydrogel product comprising crosslinked glycosaminoglycan molecules at a concentration $C_{final}$ (mg/mL), said method comprising: a) crosslinking a glycosaminoglycan having a molecular weight of above 700 kDa in conditions so as to provide a glycosaminoglycan hydrogel crosslinked by amide bonds and having a $C_{min}$ (mg/mL) that is above $C_{final}/2$, wherein $C_{min}$ is the concentration of gel-form glycosaminoglycan in the gel when fully swollen in physiological buffer; b) subjecting the hydrogel from a) to post-crosslinking degradation of the glycosaminoglycan backbone, thereby reducing the $C_{min}$ of the hydrogel to a value that is below $C_{final}/2$; and c) formulating the partially degraded hydrogel obtained from b) to form an injectable hydrogel composition having a concentration of glycosaminoglycan molecules of $C_{final}$ (mg/mL).

An alternative way of describing the above method of the first aspect and the relation of a), b), and c) therein is: a method of preparing a hydrogel product comprising crosslinked glycosaminoglycan molecules at a concentration $C_{final}$ (mg/mL), said method comprising a) crosslinking a glycosaminoglycan having a molecular weight of above 700 kDa in conditions so as to provide a glycosaminoglycan hydrogel crosslinked by amide bonds and having a first $C_{min}$ (mg/mL), wherein $C_{min}$ is the concentration of gel-form glycosaminoglycan in the gel when fully swollen in physiological buffer; b) subjecting the hydrogel from a) to post-crosslinking degradation of the glycosaminoglycan backbone, thereby reducing the first $C_{min}$ to a second $C_{min}$, and c) formulating the partially degraded hydrogel obtained from b) to form an injectable hydrogel composition having a concentration of glycosaminoglycan molecules of $C_{final}$ (mg/mL), wherein $2*$second $C_{min} < C_{final} < 2*$first $C_{min}$.

The post-crosslinking degradation of b) is a partial degradation of the glycosaminoglycan backbone.

The glycosaminoglycan (GAG) is preferably hyaluronic acid (HA). The concentration $C_{final}$ (mg/mL) is the intended concentration of the GAG in the final hydrogel product.

The inventor has found that when producing hydrogels from high molecular weight (HMW) glycosaminoglycan, such as hyaluronic acid, with the DATH/DMTMM system using low DATH loading at a range of HA concentrations during the crosslinking process, suitable gels for filler composition is initially formed, but the hydrogel may hydrolyse upon storage or during expose to degrading conditions (e.g.

heat sterilization, accelerated stability studies). This indicates that a larger number of crosslinks is needed to keep the gel intact and protect it against hydrolysis. However, increasing the amount of DATH/DMTMM—to increase the number of crosslinks in the gel—may lead to gels with high $C_{min}$ that are phase-separated at suitable GAG concentrations. In some instances, when producing gels from HMW GAGs with enough crosslinks to make them stable during autoclaving, there are difficulties in diluting the gels to 20 mg/ml (10-30 mg/ml) without obtaining phase separation. This will in turn add complexity to the process for e.g. filling the gel in syringes. Therefore, the gel is preferably homogeneous before a filling process to ensure a homogenous product. A homogeneous product is not phase separated.

The first aspect of the disclosure is based on the insight that a suitable post-crosslinking degradation that decreases the $C_{min}$ of the hydrogel makes it possible to achieve a homogeneous gel from HMW GAGs, such as HMW hyaluronic acid, crosslinked by amide bonds.

The initial crosslinking of a) of a high molecular weight GAG leads to a gel having a $C_{min}$ that is above $C_{final}/2$. $C_{min}$ is the concentration of gel-form glycosaminoglycan in the gel when fully swollen in physiological buffer. The physiological buffer may for example be 0.9% saline buffer. The buffer may also comprise 1 mM phosphate.

$C_{min}$ is a theoretical value, and a formulation where the GAG concentration is equal to $C_{min}$ would not be applicable as a product, since a hydrogel formulation with the GAG concentration equal to $C_{min}$ can easily be phase-separated in a filling/extruding process due to mechanical forces, or denoted as "phase separated" by a user. So to ensure a homogeneous gel formulation, as a potential product, the GAG concentration of the final product $C_{final}$, may be $C_{min} \times 2$ or above.

$C_{final}$ may be between 10-30 mg/mL, such as between 15-30 mg/mL, such as between 20-30 mg/mL, such as between 15-25 mg/mL, such as 20 mg/mL.

The partial degradation of the gel in b) involves mainly degradation of the glycosaminoglycan backbone, and thus only minor degradation of crosslinks between glycosaminoglycan molecules. In order to have a homogeneous gel after the post-crosslinking degradation of b), such as a gel that may be filled in syringes, $C_{min}$ of the gel after b) should be below $C_{final}/2$. Thus, a GAG product having a final concentration $C_{final}$ of 20 mg/mL is usually not homogeneous if the $C_{min}$ is above 10 mg/mL.

After the post cross-linking degradation, the GAG is still in a gel form. In c), this gel is then formulated to a final concentration $C_{final}$.

The degradation of b) can for example be acidic or alkaline. By tuning the degradation after crosslinking the HMW GAG, the inventor has thus found that it is possible, after the process, to formulate the gel to a suitable concentration for dermatological use (e.g. 10-30 mg/mL) but retain the capacity to swell in excess saline.

Starting with a GAG having a molecular weight of above 700 kDa further makes it possible to produce several different hydrogel products from the same batch of crosslinked GAG molecules, e.g. by subjecting the crosslinked GAG to different post-crosslinking degradation conditions. Thus, varying the conditions of the post-crosslinking degradation may facilitate providing hydrogel products having different molecular weight of the GAG backbone.

The method of the first aspect of the present disclosure is further a simple process without the need to isolate GAG intermediates several times. Furthermore, using a HMW GAG as starting material may be advantageous since a HMW GAG may not be as sensitive to fluctuations in molecular weight as a GAG of lower molecular weight, thus making the process more stable with increased reproducibility.

It may may be advantageous to perform the degradation after the crosslinking instead of degrading the HMW GAG before crosslinking, since degrading after crosslinking makes it easier to end up with a product having a molecular weight within a specific interval.

As a configuration of the first aspect of the disclosure, there is provided a method of preparing a hydrogel product comprising crosslinked glycosaminoglycan molecules, said method comprising: a1) crosslinking a glycosaminoglycan having a molecular weight of above 700 kDa in conditions so as to provide a glycosaminoglycan hydrogel crosslinked by amide bonds, and b1) subjecting the hydrogel from a) to post-crosslinking degradation to decrease the apparent molecular weight ($Mw_{app}$) of the crosslinked glycosaminoglycan with at least 25%, such as at least 40%, such as at least 50%.

The method may further comprise c1) of reformulating the partially degraded hydrogel obtained from b) to a final GAG concentration, $C_{final}$, of 10-30 mg/mL. Reformulation may be in PBS buffer. c1) may also comprise sterilizing the partially degraded hydrogel obtained from b1) by autoclaving to form a sterilized injectable hydrogel composition. c1) may also comprise filling the hydrogel in a syringe before sterilizing the hydrogel.

As a further configuration of the first aspect, there is provided a method of preparing a hydrogel product comprising crosslinked glycosaminoglycan molecules, said method comprising: a2) crosslinking a glycosaminoglycan having a molecular weight of above 700 kDa in conditions so as to provide a glycosaminoglycan hydrogel crosslinked by amide bonds, wherein the hydrogel is crosslinked to an extent such that it is phase-separated when diluted to $C_{final}$ (mg/mL) at pH 6.0-8.0 in 1.0 mM-20 mM phosphate buffered saline (PBS), and b2) subjecting the hydrogel from a) to post-crosslinking degradation such that the hydrogel is not phase-separated when diluted to $C_{final}$ (mg/mL) at pH 6.0-8.0 in 1.0 mM-20 mM phosphate buffer. $C_{final}$ may be as discussed herein above.

The method may further comprise c2) reformulating the partially degraded hydrogel obtained from b) to a final GAG concentration, $C_{final}$, of 10-30 mg/mL. Reformulation may be in PBS buffer. c2) may also comprise sterilizing the partially degraded hydrogel obtained from b2) by autoclaving to form a sterilized injectable hydrogel composition. c2) may also comprise filling the hydrogel in a syringe before sterilizing the hydrogel. In this configuration of the first aspect, a) may provide a hydrogel that is phase-separated when diluted to 10-30 mg/mL; such as to 20 mg/mL, at pH 6.0-8.0 in 1.0 mM-20 mM PBS, and the partial degradation of b) may lead to a hydrogel that is not phase separated at the same tested experimental conditions.

As a second aspect of the disclosure, there is provided a hydrogel product obtainable by the method of the first aspect.

Further, as a third aspect of the disclosure, there is provided a method of cosmetically treating skin, which comprises administering to the skin a hydrogel product according to the second aspect.

BRIEF DESCRIPTION OF THE FIGURES

FIG. 1 depicts a schematic of GAG crosslinking and post-crosslinking procedures.

DETAILED DESCRIPTION OF THE DISCLOSURE

Other aspects and preferred embodiments of the present disclosure is evident from the following detailed disclosure and the appended claims.

Hydrogels and Methods of Making Hydrogels

Fillers such as dermal fillers have been used to repair, restore or augment hard or soft tissue contour defects of the body due to aging, injury, or acquired or congenital deformities of the face, body and internal organs. Fillers may be natural or synthetic substances that are used to reduce wrinkles and/or fine lines, restore lost volume, hydrate the skin, soften nasolabial folds, augment and contour lips, improve scars (depressed, hypertrophic and keloid scars), strengthen weakened vocal cords, and provide other soft tissue improvements. Substances that have been utilized include fat, paraffin, human collagen, bovine collagen, silicone, hyaluronic acids, lactic acids, and glycolic acids. In 1981, a new era in soft tissue fillers emerged with the FDA approval of bovine collagen. Since then, many soft tissue fillers have emerged. The dramatic increase in the number of current and investigational fillers has been fueled by many factors including improvements in biotechnology and an emphasis on cosmetic appearance in society. With the introduction of newer fillers, there has been an ongoing need to evaluate their risk/benefit profiles and define their limitations in order to maximize patient cosmetic outcomes and safety. Common filler/hydrogel compositions include GAGs such as hyaluronic acid.

Methods of producing GAG hydrogels are disclosed in PCT publication numbers WO2017/114867, WO2017/114861, WO2017/114864, and WO2017/114865; US Pre-grant Publication Numbers US20190023812A1, US20190016830A1, US20190023855A1, and US20070066816A1; and U.S. Pat. Nos. 8,858,999, 6,831,172, 8,887,243, and, 6,703,444.

A common route for crosslinking hyaluronic acid is using a diglycidyl ether, e.g. 1,4-butanediol diglycidyl ether (BDDE). As an alternative, amide coupling using a di- or multiamine functional crosslinker together with a coupling agent is an attractive route for preparing crosslinked hyaluronic acid molecules useful for hydrogel products. For example, the use of 4-(4,6-Dimethoxy-1,3,5-triazin-2-yl)-4-methylmorpholinium chloride (DMTMM) for activation of carboxylate and subsequent condensation with a diamino structure, e.g. diaminotrehalose (DATH) has shown to be an efficient method to produce hydrogels composed of crosslinked hyaluronic acid with minor degradation of the biopolymer.

In some aspects, crosslinking is performed via crosslinkers comprising a spacer group selected from the group consisting of di-, tri-, tetra-, and oligosaccharides. This provides a hydrogel product based entirely on carbohydrate structures or derivatives thereof, which minimizes the disturbance of the crosslinking on the native properties of the GAGs utilized in producing the hydrogel.

In some aspects, the crosslinker itself contributes to maintained or increased properties of the hydrogel, for example when crosslinking with a structure that correlates to hyaluronic acid (e.g., diamino hyaluronic acid tetrasaccharide) or when crosslinking with a structure with high water retention properties (e.g., trehalose).

In some aspects, the GAG is a sulfated or non-sulfated GAG such as hyaluronan, chondroitin sulphate, heparan sulphate, heparosan, heparin, dermatan sulphate and keratan sulphate. In some aspects, the GAG is hyaluronic acid, chondroitin or chondroitin sulfate. In one aspect, the GAG is hyaluronic acid. In some aspects, the GAG is a native GAG. In some aspects, the GAG is a naturally occurring GAG. In some aspects, the GAG is used in its native state (i.e., the chemical structure of the GAG has not been altered or modified by addition of functional groups or the like). Using the GAG in its native state is preferred because this will afford a crosslinked structure more closely resembling the natural molecules, which conserves the native properties and effects of the GAG itself, and can minimize the immune response when the crosslinked GAG is introduced into the body.

In some aspects, the GAGs are covalently crosslinked. In some aspects, the covalently crosslinked GAG molecules consist of, or essentially consist of carbohydrate type structures or derivatives thereof. In some aspects, the crosslinked GAGs or hydrogels are free of, or essentially free of synthetic non-carbohydrate structures or linkers. This can be achieved by using a GAG in its native state together with a crosslinker which comprises, consists of, or essentially consist of carbohydrate type structures or derivatives thereof. In some aspects, functional groups of the crosslinker are covalently bound directly to carboxyl groups of the GAG. In some aspects, the crosslinks of the covalently crosslinked GAGs comprise, consist of, or essentially consist of di-, tri-, tetra-, and oligosaccharide spacer groups.

In some aspects, the crosslinked GAG comprises crosslinks between the GAG molecule chains, which creates a continuous network of GAG molecules held together by covalent crosslinks.

In some aspects, the crosslinked GAGs form a gel or hydrogel-water-insoluble, but substantially dilute crosslinked system of GAGs when subject to liquid, typically an aqueous liquid.

The first aspect of the disclosure relates to a method of preparing a hydrogel product comprising crosslinked glycosaminoglycan molecules at a concentration $C_{final}$ (mg/mL), said method comprising the steps of: a) crosslinking a glycosaminoglycan having a molecular weight of above 700 kDa in conditions so as to provide a glycosaminoglycan hydrogel crosslinked by amide bonds and having a $C_{min}$ (mg/mL) that is above $C_{final}/2$, wherein $C_{min}$ is the concentration of gel-form glycosaminoglycan in the gel when fully swollen in physiological buffer; b) subjecting the hydrogel from step a) to post-crosslinking degradation of the glycosaminoglycan backbone, thereby reducing the $C_{min}$ of the hydrogel to a value that is below $C_{final}/2$; and c) formulating the partially degraded hydrogel obtained from step b) to form an injectable hydrogel composition having a concentration of glycosaminoglycan molecules of $C_{final}$ (mg/mL).

In the context of the disclosure, the terms "post-crosslinking degradation", "partial degradation" and "partially degraded" have the same technical meaning.

The inventive method provides a hydrogel product. That is, it can be regarded as a water-insoluble, but substantially dilute crosslinked system of glycosaminoglycan molecules when subjected to a liquid, typically an aqueous liquid. Thus, step a) may comprise forming an insoluble gel network. The partially degraded hydrogel obtained from step b) may still be an insoluble gel network.

The produced hydrogel product contains mostly liquid by weight and can e.g. contain 90-99.9% water, but it behaves like a solid due to a three-dimensional crosslinked GAG network within the liquid. Due to its significant liquid content, the gel is structurally flexible and similar to natural tissue, which makes it very useful as a scaffold in tissue engineering and for tissue augmentation.

The partial degradation of step b) is a degradation of the GAG backbone to reduce the molecular weight of the GAG backbone present in the gel network.

In embodiments of the first aspect, the prepared hydrogel product is in a single phase, i.e. has not phase separated. Thus, the prepared hydrogel product may be a homogenous mixture.

The prepared hydrogel product is preferably biocompatible. This implies that no, or only very mild, immune response occurs in the treated individual. That is, no or only very mild undesirable local or systemic effects occur in the treated individual.

A characteristic of a gel is its capacity to absorb water until it is fully swollen.

Further addition of liquid will not dilute the gel further, i.e. the gel cannot be indefinitely diluted like a solution of free molecules. When the gel is subjected to non-precipitating conditions, it is also possible to determine its swelling degree (SwD), or inversely its minimum concentration ($C_{min}$), i.e. the hyaluronic acid concentration when the gel product is fully swollen. Harder (low-swelling) gels are generally less viscous, more elastic and expected to have a longer half-life in vivo than softer (high-swelling) gels. However, harder gels may be recognized as foreign materials by the body if they are highly chemically modified.

Step b) further comprises a partial degradation step that reduces the $C_{min}$ of the hydrogel. $C_{min}$ is the concentration of gel-form GAG in the gel when fully swollen in physiological buffer, such as in 0.9% saline.

$C_{min}$ describes the concentration of gel-form GAG in a cross-linked GAG gel product, fully swollen in 0.9% NaCl after all extractable GAG is removed. Since the product cannot absorb more liquid, this concentration is the minimum GAG concentration that can be obtained for a homogeneous hydrogel composition. For practical reasons, one skilled in the art realize that $C_{final} > C_{min}$ to avoid phase-separated gel formulations due to mechanical forces during extruding or filling. As an example, $C_{final}$ may be above $1.5 \times C_{min}$, such as above $2 \times C_{min}$.

Notably, a stronger gel will have a higher $C_{min}$, while a weaker gel will have a lower $C_{min}$.

The $C_{min}$ is determined in analogy with the determination of SwD as set out, using the relation:

$$C_{min} = \frac{1}{SwD}$$

SwD is swelling degree:

$$C_{min} = \frac{m_{fully\ swollen\ gel}}{m_{gel\text{-}form\ GAG\ in\ fully\ swollen\ gel}}$$

SwD is preferably expressed in g/g, mL/g, or as a dimensionless number. SwD is the inverted concentration of gel-form GAG in a gel that is fully swollen in 0.9% saline, i.e. the volume, or mass, of fully swollen gel that can be formed per gram dry cross-linked GAG. SwD describes the maximum liquid-absorbing (0.9% saline) capability of the product.

The $C_{min}$ is the minimum theoretical GAG concentration, which is the concentration of gel-form GAG in a gel that is fully swollen in 0.9% saline, normally expressed in mg/g or mg/mL.

$$C_{min}^{-1} = SwD$$

The $C_{final}$ is the intended concentration of the GAG in the final hydrogel product. $C_{final}$ is preferably more than $2 \times C_{min}$.

In embodiments of the first aspect of the disclosure, the glycosaminoglycan hydrogel crosslinked by amide bonds provided in step a) has a $C_{min}$ of at least 10 mg/mL, such as at least 15 mg/mL, such as at least 20 mg/mL, such as between 20-50 mg/mL.

In some embodiments, the GAG hydrogel crosslinked by amide bonds provided in step a) has a $C_{min}$ of between 10 to 60 mg/mL, 15 to 60 mg/mL, 20 to 60 mg/mL, 25 to 60 mg/mL, 30 to 60 mg/mL, 35 to 60 mg/mL, 40 to 60 mg/mL, 45 to 60 mg/mL, 50 to 60 mg/mL, 55 to 60 mg/mL, 10 to 55 mg/mL, 15 to 55 mg/mL, 20 to 55 mg/mL, 25 to 55 mg/mL, 30 to 55 mg/mL, 35 to 55 mg/mL, 40 to 55 mg/mL, 45 to 55 mg/mL, 50 to 55 mg/mL, 10 to 50 mg/mL, 15 to 50 mg/mL, 20 to 50 mg/mL, 25 to 50 mg/mL, 30 to 50 mg/mL, 35 to 50 mg/mL, 40 to 50 mg/mL, 45 to 50 mg/mL, 10 to 45 mg/mL, 15 to 45 mg/mL, 20 to 45 mg/mL, 25 to 45 mg/mL, 30 to 45 mg/mL, 35 to 45 mg/mL, 40 to 45 mg/mL, 10 to 35 mg/mL, 15 to 35 mg/mL, 20 to 35 mg/mL, 25 to 35 mg/mL, 30 to 35 mg/mL, 10 to 30 mg/mL, 15 to 30 mg/mL, 20 to 30 mg/mL, 25 to 30 mg/mL, 10 to 25 mg/mL, 15 to 25 mg/mL, 20 to 25 mg/mL, 10 to 20 mg/mL, 15 to 20 mg/mL, or 10 to 15 mg/mL.

In some embodiments, the GAG hydrogel crosslinked by amide bonds provided in step a) has a $C_{min}$ of at least 10 mg/mL, at least 11 mg/mL, at least 12 mg/mL, at least 13 mg/mL, at least 14 mg/mL, at least 15 mg/mL, at least 16 mg/mL, at least 17 mg/mL, at least 18 mg/mL, at least 19 mg/mL, at least 20 mg/mL, at least 21 mg/mL, at least 22 mg/mL, at least 23 mg/mL, at least 24 mg/mL, at least 25 mg/mL, at least 26 mg/mL, at least 27 mg/mL, at least 28 mg/mL, at least 29 mg/mL, at least 30 mg/mL, at least 32 mg/mL, at least 34 mg/mL, at least 36 mg/mL, at least 38 mg/mL, at least 40 mg/mL, at least 42 mg/mL, at least 44 mg/mL, at least 46 mg/mL, at least 48 mg/mL, at least 50 mg/mL, at least 52 mg/mL, at least 54 mg/mL, at least 56 mg/mL, at least 58 mg/mL, or at least 60 mg/mL.

In embodiments of the first aspect of the disclosure, the $C_{min}$ of the hydrogel is reduced to, in step b), between 1 to 15 mg/mL. In some embodiments, of the first aspect of the disclosure, the $C_{min}$ of the hydrogel is reduced to, in step b), between 1 to 15 mg/mL, 2 to 15 mg/mL, 3 to 15 mg/mL, 4 to 15 mg/mL, 5 to 15 mg/mL, 6 to 15 mg/mL, 7 to 15 mg/mL, 8 to 15 mg/mL, 9 to 15 mg/mL, 10 to 15 mg/mL, 11 to 15 mg/mL, 12 to 15 mg/mL, 13 to 15 mg/mL, 14 to 15 mg/mL, between 1 to 14 mg/mL, 2 to 14 mg/mL, 3 to 14 mg/mL, 4 to 14 mg/mL, 5 to 14 mg/mL, 6 to 14 mg/mL, 7 to 14 mg/mL, 8 to 14 mg/mL, 9 to 14 mg/mL, 10 to 14 mg/mL, 11 to 14 mg/mL, 12 to 14 mg/mL, 13 to 14 mg/mL, between 1 to 13 mg/mL, 2 to 13 mg/mL, 3 to 13 mg/mL, 4 to 13 mg/mL, 5 to 13 mg/mL, 6 to 13 mg/mL, 7 to 13 mg/mL, 8 to 13 mg/mL, 9 to 13 mg/mL, 10 to 13 mg/mL, 11 to 13 mg/mL, 12 to 13 mg/mL, between 1 to 12 mg/mL, 2 to 12 mg/mL, 3 to 12 mg/mL, 4 to 12 mg/mL, 5 to 12 mg/mL, 6 to 12 mg/mL, 7 to 12 mg/mL, 8 to 12 mg/mL, 9 to 12 mg/mL, 10 to 12 mg/mL, 11 to 12 mg/mL, between 1 to 11 mg/mL, 2 to 11 mg/mL, 3 to 11 mg/mL, 4 to 11 mg/mL, 5 to 11 mg/mL, 6 to 11 mg/mL, 7 to 11 mg/mL, 8 to 11 mg/mL, 9 to 11 mg/mL, 10 to 11 mg/mL, between 1 to 10 mg/mL, 2 to 10 mg/mL, 3 to 10 mg/mL, 4 to 10 mg/mL, 5 to 10 mg/mL, 6 to 10 mg/mL, 7 to 10 mg/mL, 8 to 10 mg/mL, 9 to 10 mg/mL, between 1 to 9 mg/mL, 2 to 9 mg/mL, 3 to 9 mg/mL, 4 to 9 mg/mL, 5 to 9 mg/mL, 6 to 9 mg/mL, 7 to 9 mg/mL, 8 to 9 mg/mL, between 1 to 8 mg/mL, 2 to 8 mg/mL, 3 to 8 mg/mL, 4 to 8 mg/mL, 5 to 8 mg/mL, 6 to 8 mg/mL, 7 to 8 mg/mL, between 1 to 7 mg/mL, 2 to 7 mg/mL, 3 to 7 mg/mL, 4 to 7 mg/mL, 5 to 7 mg/mL, 6 to 7 mg/mL, between 1 to 6 mg/mL, 2 to 6 mg/mL, 3 to 6 mg/mL, 4 to 6 mg/mL, 5 to 6 mg/mL, between 1 to 5 mg/mL, 2 to 5 mg/mL, 3 to 5 mg/mL, 4 to 5 mg/mL, between 1 to 4 mg/mL, 2 to 4 mg/mL, 3 to 4 mg/mL, between 1 to 3 mg/mL, 2 to 3 mg/mL, between 1 to 2 mg/mL.

In embodiments of the first aspect of the disclosure, the $C_{min}$ of the hydrogel is reduced to a value that is above 0.5 mg/mL, such as between 0.5-15 mg/mL, such as between 1.0-10 mg/mL, such as between 2-10 mg/mL, in step b).

In embodiments of the first aspect of the disclosure, $C_{final}$, i.e. the final concentration of the hydrogel product, is above 10 mg/mL, such as between 10-30 mg/mL, such as between 15-25 mg/mL.

Furthermore, in embodiments of the first aspect of the disclosure, the $C_{min}$ of the hydrogel is reduced by at least 1 mg/mL, such as at least 5 mg/mL, such as between 1-50 mg/mL, such as between 5-10 mg/mL, in step b).

In some embodiments, of the first aspect of the disclosure, the $C_{min}$ of the hydrogel is reduced to, in step b), 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, or 15 mg/mL.

Furthermore, in embodiments of the first aspect of the disclosure, the $C_{min}$ of the hydrogel is reduced by at least 5%, such as by at least 10%, such as by at least 25%, in step b). In some embodiments, the $C_{min}$ of the hydrogel is reduced by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, in step b).

In embodiments of the first aspect of the disclosure, the post-crosslinking degradation of step b) decreases the apparent molecular weight ($Mw_{app}$) of the crosslinked glycosaminoglycan by at least 25%. As an example, the post-crosslinking degradation may lead to a decrease in ($Mw_{app}$) that is at least 30%, such as at least 40%, such as at least 50%. In some embodiments the post-crosslinking degradation leads to a decrease in ($Mw_{app}$) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%.

Step c) comprises formulating, or reconstituting, the partially degraded hydrogel obtained from step b) to form an injectable hydrogel composition having a concentration of glycosaminoglycan molecules of $C_{final}$ (mg/mL).

Hydrogel products, such as hyaluronic acid based hydrogel compositions, for use in injection need to be sterilized before use. Sterilization is generally performed by heat treatment, such as autoclaving. Thus, step c) may also comprise sterilizing the partially degraded hydrogel obtained from step b) by autoclaving to form a sterilized injectable hydrogel composition.

Thus, the partially degraded hydrogel obtained from step b) may also be filled in syringes and thereafter subjected to sterilization by autoclaving to form a sterilized injectable hydrogel composition.

In some embodiments, the sterilizing step may lead to a further degradation of the crosslinked GAG.

The hydrogel product may thus be an injectable hydrogel composition. The term "injectable" means that the composition is provided in a form which is suitable for parenteral injection, e.g. into soft tissue, such as skin, of a subject or patient.

An injectable composition should be sterile and free from components that may cause adverse reactions when introduced into soft tissue, such as the skin, of a subject or patient. This implies that no, or only very mild, immune response occurs in the treated individual. That is, no or only very mild undesirable local or systemic effects occur in the treated individual.

Sterilization of the hydrogel product may be performed by autoclaving, i.e. sterilization using saturated steam. The autoclaving may be performed at an $F_0$-value>4. The autoclaving may preferably be performed at an $F_0$-value in the range of 10 to 50, such as in the range of 20-30. The $F_0$ value of a saturated steam sterilization process is the lethality expressed in terms of the equivalent time in minutes at a temperature of 121° C. delivered by the process to the product in its final container with reference to microorganisms possessing a Z-value of 10.

Furthermore, the concentration of the GAG in the gel may be set to a desired value prior to sterilization. Thus, in embodiments of the first aspect, step c) comprises a step of adjusting the concentration of the partially degraded hydrogel to a concentration that is at least $2.0 \times C_{min}$, at least $2.1 \times C_{min}$, at least $2.2 \times C_{min}$, at least $2.3 \times C_{min}$, at least $2.4 \times C_{min}$, at least $2.5 \times C_{min}$, at least $2.6 \times C_{min}$, at least $2.7 \times C_{min}$, at least $2.8 \times C_{min}$, at least $2.9 \times C_{min}$, at least $3.0 \times C_{min}$, at least $3.5 \times C_{min}$, at least $4.0 \times C_{min}$, at least $4.5 \times C_{min}$, at least $5.0 \times C_{min}$, at least $5.5 \times C_{min}$, at least $6.0 \times C_{min}$, at least $6.5 \times C_{min}$, at least $7.0 \times C_{min}$, at least $7.5 \times C_{min}$, at least $8.0 \times C_{min}$, at least $8.5 \times C_{min}$, at least $9.0 \times C_{min}$, at least $10.0 \times C_{min}$, at least $10.5 \times C_{min}$, or at least $11.0 \times C_{min}$, before filling in syringes and an optional step of sterilizing.

Thus, $C_{final}$ of the hydrogel that is subjected to filling in syringes in step c) may be at least $1.5 \times C_{min}$, at least $1.6 \times C_{min}$, at least $1.7 \times C_{min}$, at least $1.8 \times C_{min}$, at least $1.9 \times C_{min}$, at least $2.0 \times C_{min}$, at least $2.1 \times C_{min}$, at least $2.2 \times C_{min}$, at least $2.3 \times C_{min}$, at least $2.4 \times C_{min}$, at least $2.5 \times C_{min}$, at least $2.6 \times C_{min}$, at least $2.7 \times C_{min}$, at least $2.8 \times C_{min}$, at least $2.9 \times C_{min}$, or at least $3.0 \times C_{min}$. In some aspects, this is advantageous since this may lead to a product that is not phase separated.

The apparent molecular weight ($Mw_{app}$) of the gel network is a simulated value of the expected molecular weight of the polymer within the gel network. This is obtained by exposure of the polymer to the process/steps but removing one parameter/reagent, with minor effect with respect to reduction of the Mw, to avoid crosslinking and subsequently enable determination of the Mw. Determination of molecular weight in a gel network is not possible.

In embodiments of the first aspect of the disclosure, the hydrogel in step a) is crosslinked to an extent such that it is phase-separated when diluted to 20 mg/ml at pH 6.0-8.0 in 1.0 mM-20 mM phosphate buffer and wherein the post-crosslinking degradation of step b) is to an extent such that the hydrogel is not phase-separated when diluted to 20 mg/ml at pH 6.0-8.0 in 1.0 mM-20 mM phosphate buffer. In some aspects, the phosphate buffer is PBS.

A hydrogel being phase separated refers to the hydrogel comprising at least two distinct phases, such as an aqueous phase and a phase of high GAG concentration.

The crosslinking of step a) may thus be to such an extent that the gel is phase-separated when diluted to 20 mg/ml at pH 6.0-8.0 in 1.0 mM-20 mM PBS, which is suitable formulation conditions of an injectable product. However, the partial degradation of step b) may then lead to a product that is not phase-separated when diluted to 20 mg/ml at pH 6.0-8.0 in 1.0 mM-20 mM phosphate buffer. Thus, after the partial degradation of step b), the hydrogel is suitable for being formulated into an injectable product.

It is to be understood that neither step a) or step b) necessarily comprises a step of diluting the GAG to 20 mg/ml at pH 6.0-8.0 in 1.0 mM-20 mM PBS.

However, in embodiments of the first aspect of the disclosure, the method further comprises a step of formulating and/or diluting the partially degraded hydrogel from step b) to 10-30 mg/mL, such as to about 20 mg/mL at pH 6.0-8.0 in 1.0 mM-20 mM PBS.

According to certain embodiments, the glycosaminoglycan is selected from the group consisting of hyaluronic acid, heparosan, chondroitin and chondroitin sulfate, and mixtures thereof. According to some embodiments, the glycosaminoglycan is selected from the group consisting of hyaluronic acid, chondroitin and chondroitin sulfate, and mixtures thereof. In a preferred embodiment, the glycosaminoglycan is hyaluronic acid.

Unless otherwise provided, the term "hyaluronic acid" encompasses all variants and combinations of variants of hyaluronic acid, hyaluronate or hyaluronan, of various chain lengths and charge states, as well as with various chemical modifications, including crosslinking. That is, the term also encompasses the various hyaluronate salts of hyaluronic acid with various counter ions, such as sodium hyaluronate. Various modifications of the hyaluronic acid are also encompassed by the term, such as oxidation, e.g. oxidation of —$CH_2OH$ groups to —CHO and/or —COOH; periodate oxidation of vicinal hydroxyl groups, optionally followed by reduction, e.g. reduction of —CHO to —$CH_2OH$ or coupling with amines to form imines followed by reduction to secondary amines; sulphation; deamidation, optionally followed by deamination or amide formation with new acids; esterification; crosslinking; substitutions with various compounds, e.g. using a crosslinking agent or a carbodiimide assisted coupling; including coupling of different molecules, such as proteins, peptides and active drug components, to hyaluronic acid; and deacetylation. Other examples of modifications are isourea, hydrazide, bromocyan, monoepoxide and monosulfone couplings. The hyaluronic acid can be obtained from various sources of animal and non-animal origin. Sources of non-animal origin include yeast and preferably bacteria. The molecular weight of a single hyaluronic acid molecule is typically in the range of 0.1-10 MDa, but other molecular weights are possible.

According to the inventive method, the GAG that is crosslinked in step a) has a molecular weight of above 700 kDa. GAGs of 700 kDA and above are considered as a high-molecular weight (HMW) GAG. As an example, the GAG that is crosslinked in step a) has a molecular weight of above 800 kDa, such as above 900 kDa, such as about 1 MDa, such as above 1 MDa, such as about or above 3 MDa. As an example, the GAG that is crosslinked in step a) may be hyaluronic acid having a molecular weight of above 800 kDa, such as above 900 kDa, such as about 1 MDa, such as about 3 MDa.

In some aspects, the GAG has a molecular weight of above 700 kDa, 800 kDa, 900 kDa, 1000 kDa, 1100 kDa, 1200 kDa, 1300 kDa, 1400 kDa, 1500 kDa, 1600 kDa, 1700 kDa, 1800 kDa, 1900 kDa, 2000 kDa, 2500 kDa, 3000 kDa, 3500 kDa, 4000 kDa, 4500 kDa, 5000 kDa, 5500 kDa, 6000 kDa, 6500 kDa, 7000 kDa, 7500 kDa, 8000 kDa, 8500 kDa, 9000 kDa, 9500 kDa, or 10000 kDa.

In some aspects, the GAG has a molecular weight of above about 200 kDa, about 300 kDa, about 400 kDa, about 500 kDa, about 600 kDa, about 700 kDa, about 800 kDa, about 900 kDa, about 1000 kDa, about 1100 kDa, about 1200 kDa, about 1300 kDa, about 1400 kDa, about 1500 kDa, about 1600 kDa, about 1700 kDa, about 1800 kDa, about 1900 kDa, about 2000 kDa, about 2500 kDa, about 3000 kDa, about 3500 kDa, about 4000 kDa, about 4500 kDa, about 5000 kDa, about 5500 kDa, about 6000 kDa, about 6500 kDa, about 7000 kDa, about 7500 kDa, about 8000 kDa, about 8500 kDa, about 9000 kDa, about 9500 kDa, or about 10000 kDa.

In certain embodiments the concentration of the glycosaminoglycan in the prepared hydrogel product obtained is in the range of 1 to 100 mg/mL. In some embodiments the concentration of the glycosaminoglycan of the prepared hydrogel is in the range of 2 to 50 mg/mL. In specific embodiments the concentration of the glycosaminoglycan is in the range of 5 to 30 mg/mL or in the range of 10 to 30 mg/mL.

In embodiments of the first aspect of the disclosure, the concentration of the GAG during crosslinking in step a) is 50-300 mg/mL. In some aspects, the concentration of the GAG during crosslinking in step a) is 50-75 mg/mL, 50-100 mg/mL, 50-150 mg/mL, 50-200 mg/mL, 50-300 mg/mL, 60-75 mg/mL, 60-100 mg/mL, 60-150 mg/mL, 60-200 mg/mL, 60-300 mg/mL, 75-100 mg/mL, 75-150 mg/mL, 75-200 mg/mL, 75-300 mg/mL, 100-150 mg/mL, 100-200 mg/mL, 100-300 mg/mL, 150-200 mg/mL, 150-300 mg/mL, or 200-300 mg/mL.

Further, in embodiments of the first aspect of the disclosure, the crosslinking of step a) is performed at a GAG concentration of at least at least 50 mg/mL, at least 60 mg/mL, at least 75 mg/mL, at least 100 mg/mL, at least 125 mg/mL, at least 150 mg/mL, at least 175 mg/mL, at least 200 mg/mL, at least 225 mg/mL, at least 250 mg/mL, at least 275 mg/mL, or at least 300 mg/mL.

Step a) comprises crosslinking of the GAG so as to provide a glycosaminoglycan hydrogel crosslinked by amide bonds. Thus, the GAG provided in step a) is covalently crosslinked by amide bonds. Furthermore, the crosslinking of step a) may be performed at a pH of 5.0-9.0, preferably at a pH of 6.0-8.0. Thus, the crosslinking of step a) may be performed at neutral conditions.

The hydrogel crosslinked by amide bonds may be crosslinked so at least 90%, such as at least 95%, such as at least 99% of the crosslinks in the gel are amide bonds. In some aspects, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of the crosslinks in the gel are amide bonds.

The amide crosslinked glycosaminoglycan may be obtained by covalently crosslinking a glycosaminoglycan using a bi- or polyfunctional crosslinking agent, or it may be obtained by so called linker free crosslinking where a coupling agent is used to form covalent bonds directly between functional groups already present in the glycosaminoglycan, but where the coupling agent does not form part of the crosslink. Amide coupling using a di- or multiamine functional crosslinker together with a coupling agent is an attractive route to preparing crosslinked glycosaminoglycan molecules useful for hydrogel products. Amide crosslinking can be achieved using a non-carbohydrate based di- or multinucleophile crosslinker, for example hexamethylenediamine (HMDA), or a carbohydrate based di- or multinucleophile crosslinker, for example diaminotrehalose (DATH) together with a glycosaminoglycan.

In embodiments, the crosslinking of step a) comprises a1) providing a solution of glycosaminoglycan molecules; a2) activating carboxyl groups on the glycosaminoglycan molecules with a coupling agent to form activated glycosaminoglycan molecules; a3) crosslinking the activated glycosaminoglycan molecules via their activated carboxyl groups using a di- or multinucleophile functional crosslinker comprising a spacer group selected from the group consisting of di-, tri-, tetra-, and oligosaccharides to obtain crosslinked glycosaminoglycan molecules.

The free amine groups of the deacetylated glycosaminoglycan may be coupled to carboxylate groups on the glycosaminoglycan to form amide groups. The coupling may be performed using a coupling agent that facilitate the amide coupling but does not itself form part of the crosslinked product. The coupling agent may for example be selected from the group consisting of triazine-based coupling agents, carbodiimide coupling agents, imidazolium-derived coupling reagents, Oxyma and COMU. As an example, the coupling agent may be a peptide coupling agent.

A preferred coupling agent is a triazine-based coupling agent, including the group consisting of 4-(4,6-dimethoxy-1,3,5-triazin-2-yl)-4-methylmorpholinium chloride (DMTMM) and 2-chloro-4,6-dimethoxy-1,3,5-triazine (CDMT), preferably DMTMM. Another preferred coupling agent is a carbodiimide coupling agent, preferably N-(3-dimethylaminopropyl)-N'-ethylcarbodiimide (EDC) combined with N-hydroxysuccinimide (NHS).

As an example, the coupling agent may be 4-(4,6-dimethoxy-1,3,5-triazin-2-yl)-4-methylmorpholinium chloride (DMTMM, also known as DMT-MM or MMTM).

DMTMM facilitates the amide coupling but does not itself form part of the produced crosslinked glycosaminoglycan.

Crosslinking of the glycosaminoglycan in step a) may for example be achieved in aqueous media using a crosslinker comprising at least two nucleophilic functional groups, for example amine groups, capable of forming covalent bonds directly with carboxylic acid groups of GAG molecules by a reaction involving the use of a coupling agent.

The crosslinker comprising at least two nucleophilic functional groups may for example be a non-carbohydrate based di- or multinucleophilic crosslinker or a carbohydrate based di- or multinucleophilic crosslinker.

Carbohydrate based di- or multinucleophilic crosslinkers are preferred, since they provide a hydrogel product based entirely on carbohydrate type structures or derivatives thereof, which minimizes the disturbance of the crosslinking on the native properties of the glycosaminoglycans. The crosslinker itself can also contribute to maintained or increased properties of the hydrogel, for example when crosslinking with a structure that correlates to hyaluronic acid or when crosslinking with a structure with high water retention properties.

The carbohydrate based di- or multinucleophilic crosslinker may for example be selected from the group consisting of di- or multinucleophilic functional di-, tri-, tetra-, oligosaccharides, and polysaccharides.

As an example, the nucleophilic groups of the di- or multinucleophile functional crosslinker used in step a3) may be selected from the group consisting of primary amine, hydrazine, hydrazide, carbazate, semi-carbazide, thiosemi-carbazide, thiocarbazate and aminoxy. Furthermore, the spacer group of the di- or multinucleophile functional crosslinker used in step a3) may be selected from di-, tri-, and tetrasaccharides.

As an example, the crosslinker may be diaminotrehalose (DATH). Diaminotrehalose (DATH) can be synthesized as described in "*Synthetic Carbohydrate Polymers Containing Trehalose Residues in the Main Chain: Preparation and Characteristic Properties*"; Keisuke Kurita,* Naoko Masuda, Sadafumi Aibe, Kaori Murakami, Shigeru Ishii, and Shin-Ichiro Nishimurat; *Macromolecules* 1994, 27, 7544-7549.

DATH may advantageously be used together with DMTMM as coupling agent.

The post-crosslinking degradation of step b) may have little effect on the crosslinking ratio (CrR) of the crosslinked gel. The CrR may be a measured property of an amide crosslinked gel that has been crosslinked using a di- or multinucleophile functional crosslinker. The CrR may be analyzed with LC-SEC-MS and defined as:

$$CrR = \frac{\text{mol crosslinked crosslinker with amide bonds}}{\text{mol linked crosslinker with amide bonds}}$$

A CrR of 1.0 means that all of the crosslinker has crosslinked. Thus, in embodiments, the post-crosslinking degradation of step b) involves reducing the effective crosslinking degree (CrR) of the glycosaminoglycan less than 10%, such as less than 5%.

The method of preparing a hydrogel product by crosslinking glycosaminoglycan molecules by amide bonds, may also be achieved by using an activating agent for the carboxyl groups on the glycosaminoglycan molecule backbone and amino groups of an at least partially deacetylated glycosaminoglycan. Crosslinking according to the inventive method can be achieved by mild and efficient routes resulting in high yields with minimal degradation of the glycosaminoglycan molecules.

Consequently, crosslinking to form an amide crosslinked hydrogel can also be achieved using an at least partially deacetylated glycosaminoglycan, either alone or in combination with a second glycosaminoglycan, whereby the deacetylated glycosaminoglycan itself acts as the di- or multinucleophile crosslinker. Thus, in embodiments, the di- or multinucleophilic crosslinker is an at least partially deacetylated glycosaminoglycan, i.e. an acetylated glycosaminoglycan which has been at least partially deacetylated to provide a glycosaminoglycan having free amine groups.

An at least partially deacetylated glycosaminoglycan may be a glycosaminoglycan in which significant portion of the N-acetyl groups of the glycosaminoglycan, particularly at least 1%, preferably at least 2%, at least 3%, at least 4%, or at least 5%, of the N-acetyl groups have been converted to free amine groups. More preferably, at least 3% of the N-acetyl groups of the glycosaminoglycan may have been converted to free amine groups.

According to some embodiments, the at least partially deacetylated glycosaminoglycan has a degree of acetylation of 99% or less, preferably 98% or less, preferably 97% or less, preferably 96% or less, preferably 95% or less, preferably 94% or less, preferably 93% or less. In some embodiments, the crosslinked glycosaminoglycan provided in step a) has a Degree of Acetylation of at least 75%, such as at least 80%, such as at least 85%, such as at least 90%.

As an example, the crosslinking of step a) may comprise crosslinking an at least partially N-deacetylated glycosaminoglycan by amide bonds between carboxyl groups and free amine groups on the glycosaminoglycan backbone to provide the glycosaminoglycan hydrogel crosslinked by amide bonds.

In other embodiments, the crosslinked GAG is obtained by: i) crosslinking at least partially deacetylated GAG to partially deacetylated GAG in the presence of a coupling agent using free amine and carboxylic acid groups present in the at least partially deacetylated GAGs; or ii) crosslinking at least partially deacetylated GAG to a non-deacetylated GAG in the presence of a coupling agent using free amine groups present in the at least partially deacetylated GAG and carboxylic acid groups present in the GAG.

Crosslinking glycosaminoglycans directly via formation of amide bonds between amino and carboxyl groups present on the glycosaminoglycans provides a hydrogel product based entirely on carbohydrate type structures. This minimizes the disturbance of the crosslinking on the native properties of the glycosaminoglycans.

The post-crosslinking degradation of step b) may have no or little effect on the crosslinking degree of the GAG. The crosslinking degree (CrD) may be a measured property of an amide crosslinked gel that has been crosslinked using deacetylated GAG for forming the amide bonds. The post-crosslinking degradation of step b) may thus mainly involve degradation of the polymer backbone with little effect on the crosslinks. Thus, in embodiments of the first aspect, the post-crosslinking degradation of step b) involves reducing the crosslinking degree (CrD) of the glycosaminoglycan less than 10%, such as less than 5%. The crosslinking degree CrD may be analyzed with SEC-MS and be defined as:

$$CrD_{amide} = \frac{n_{amide\ crosslinks}}{n_{(HA\ disaccharides)}}$$

$$CrD_{amide} = \frac{\sum(\text{Area amid crosslinked } HA \text{ fragments})}{\sum(\text{Area amid crosslinked } HA \text{ fragments} +} *(100 - DoA)$$

In an embodiment, the crosslinked glycosaminoglycan of the composition is present in the form of a crosslinked hyaluronic acid crosslinked by a crosslinking agent, wherein the concentration of said hyaluronic acid is in the range of 2 to 50 mg/mL and the degree of modification with said crosslinking agent is in the range of 0.1 to 2 mole %.

The post-crosslinking degradation of step b) may be performed in alkaline or acid conditions. As an example, the post-crosslinking degradation of step b) is performed in alkaline or acid conditions for at least 2 hours, such as for at least 10 hours, such as for at least 15 hours, such as for at least 20 hours, such as for at least 24 hours, such as up to 49 hours. For example, the post-crosslinking degradation may be performed by addition of NaOH, such as 1.0 M NaOH or an acid.

As an example, the partial degradation may be performed by addition of 0.25-3.0 NaOH and the degradation may continue for 2-48 hours. As an example, the post-crosslinking degradation may be performed by addition of 0.25-3.0 NaOH and the degradation may continue for 24 hours.

In some embodiments, the partial degradation or post-crosslinking degradation may be performed by addition of 0.25 M NaOH, 0.3 M NaOH, 0.35 M NaOH, 0.4 M NaOH, 0.45 M NaOH, 0.5 M NaOH, 0.55 M NaOH, 0.6 M NaOH, 0.65 M NaOH, 0.7 M NaOH, 0.75 M NaOH, 0.8 M NaOH, 0.85 M NaOH, 0.9 M NaOH, 0.95 M NaOH, 1.1 M NaOH, 1.2 M NaOH, 1.3 M NaOH, 1.4 M NaOH, 1.5 M NaOH, 1.6 M NaOH, 1.7 M NaOH, 1.8 M NaOH, 1.9 M NaOH, 2 M NaOH, 2.1 M NaOH, 2.3 M NaOH, 2.4 M NaOH, 2.5 M NaOH, 2.6 M NaOH, 2.7 M NaOH, 2.8 M NaOH, 2.9 M NaOH, or 3.0 M NaOH.

As an example, the post-crosslinking degradation may be performed by addition of acid, such as HCl, $H_2SO_4$ or methanesulfonic acid (MsOH).

The post-crosslinking degradation of step b) may further be performed at room temperature, or elevated temperature such as 30° C., such as 40° C.

The post-crosslinking degradation of step b) may be performed in alkaline or acid conditions for about 24 hours at room temperature.

In some embodiments, the post-crosslinking degradation of step b) may be performed at room temperature, or elevated temperatures such as 30° C., such as 40° C. for 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, or 48 hours.

In some embodiments, the post-crosslinking degradation of step b) may be performed at room temperature, or elevated temperatures such as 30° C., such as 40° C. for at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, or at least 48 hours.

In some embodiments, the post-crosslinking degradation of step b) may be performed at room temperature, or elevated temperatures such as 30° C., such as 40° C. for between 2 to 48 hours, 2 to 42 hours, 2 to 38 hours, 2 to 34 hours, 2 to 30 hours, 2 to 26 hours, 2 to 24 hours, 2 to 22 hours, 2 to 20 hours, 2 to 18 hours, 2 to 16 hours, 2 to 14 hours, 2 to 12 hours, 2 to 10 hours, 2 to 8 hours, 2 to 6 hours, 2 to 4 hours, 4 to 48 hours, 4 to 42 hours, 4 to 38 hours, 4 to 34 hours, 4 to 30 hours, 4 to 26 hours, 4 to 24 hours, 4 to 22 hours, 4 to 20 hours, 4 to 18 hours, 4 to 16 hours, 4 to 14 hours, 4 to 12 hours, 4 to 10 hours, 4 to 8 hours, 4 to 6 hours, 6 to 48 hours, 6 to 42 hours, 6 to 38 hours, 6 to 34 hours, 6 to 30 hours, 6 to 26 hours, 6 to 24 hours, 6 to 22 hours, 6 to 20 hours, 6 to 18 hours, 6 to 16 hours, 6 to 14 hours, 6 to 12 hours, 6 to 10 hours, 6 to 8 hours, 8 to 48 hours, 8 to 42 hours, 8 to 38 hours, 8 to 34 hours, 8 to 30 hours, 8 to 26 hours, 8 to 24 hours, 8 to 22 hours, 8 to 20 hours, 8 to 18 hours, 8 to 16 hours, 8 to 14 hours, 8 to 12 hours, 8 to 10 hours, 10 to 48 hours, 10 to 42 hours, 10 to 38 hours, 10 to 34 hours, 10 to 30 hours, 10 to 26 hours, 10 to 24 hours, 10 to 22 hours, 10 to 20 hours, 10 to 18 hours, 10 to 16 hours, 10 to 14 hours, 10 to 12 hours, 12 to 48 hours, 12 to 42 hours, 12 to 38 hours, 12 to 34 hours, 12 to 30 hours, 12 to 26 hours, 12 to 24 hours, 12 to 22 hours, 12 to 20 hours, 12 to 18 hours, 12 to 16 hours, 12 to 14 hours, 14 to 48 hours, 14 to 42 hours, 14 to 38 hours, 14 to 34 hours, 14 to 30 hours, 14 to 26 hours, 14 to 24 hours, 14 to 22 hours, 14 to 20 hours, 14 to 18 hours, 14 to 16 hours, 16 to 48 hours, 16 to 42 hours, 16 to 38 hours, 16 to 34 hours, 16 to 30 hours, 16 to 26 hours, 16 to 24 hours, 16 to 22 hours, 16 to 20 hours, 16 to 18 hours, 18 to 48 hours, 18 to 42 hours, 18 to 38 hours, 18 to 34 hours, 18 to 30 hours, 18 to 26 hours, 18 to 24 hours, 18 to 22 hours, 18 to 20 hours, 20 to 48 hours, 20 to 42 hours, 20 to 38 hours, 20 to 34 hours, 20 to 30 hours, 20 to 26 hours, 2 to 24 hours, 2 to 22 hours, 20 to 48 hours, 20 to 42 hours, 20 to 38 hours, 20 to 34 hours, 20 to 30 hours, 20 to 26 hours, 20 to 24 hours, 24 to 48 hours, 24 to 42 hours, 24 to 38 hours, 24 to 34 hours, 24 to 30 hours, 24 to 26 hours, 26 to 48 hours, 26 to 42 hours, 26 to 38 hours, 26 to 34 hours, 26 to 30 hours, 30 to 48 hours, 30 to 42 hours, 30 to 38 hours, 30 to 34 hours, 34 to 48 hours, 34 to 42 hours, 34 to 38 hours, 38 to 48 hours, 38 to 42 hours, or 42 to 48 hours.

As a second aspect of the disclosure there is provided a hydrogel product obtainable by the method according to the first aspect described above.

The hydrogel product may be a sterilized injectable hydrogel composition, such as a sterilized injectable hydrogel composition provided in the form of a pre-filled syringe, i.e. a syringe that is pre-filled with the injectable hydrogel composition and autoclaved.

Such a sterilized injectable hydrogel composition may advantageously be used for the transport or administration and slow or controlled release of various pharmaceutical or cosmetic substances. The sterilized injectable hydrogel composition may be employed in medical as well as non-medical, e.g. purely cosmetic, procedures by injection of the composition into soft tissues of a patient or subject. The compositions may be useful in, e.g., soft tissue augmentation, for example filling of wrinkles, by hyaluronic acid gel injection. The compositions may be useful in a cosmetic treatment, referred to herein as skin revitalization, whereby small quantities of a hyaluronic acid composition are injected into the dermis at a number of injection sites distributed over an area of the skin to be treated, resulting in improved skin tone and skin elasticity. Skin revitalization is a simple procedure and health risks associated with the procedure are very low.

A hydrogel product, such as a hydrogel composition, may be used for example in the treatment of various dermatological conditions. Particularly, there is provided an injectable hyaluronic acid composition as described above for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteatotic eczema. In other words, there is provided an injectable hyaluronic acid composition as described above for use in the manufacture of a medicament for use in a dermatological treatment selected from the group consisting of wound healing, treatment of dry skin conditions or sun-damaged skin, treatment of hyper pigmentation disorders, treatment and prevention of hair loss, and treatment of conditions that have inflammation as a component of the disease process, such as psoriasis and asteatotic eczema.

According to other aspects illustrated herein, there is provided the use of an injectable hyaluronic acid composition as described above for cosmetic, non-medical, treatment of a subject by injection of the composition into the skin of the subject. As a further aspect of the disclosure, there is provided a method of cosmetically treating skin, which comprises administering to the skin a hydrogel product according to the second aspect above.

A purpose of the cosmetic, non-medical, treatment may be for improving the appearance of the skin, preventing and/or treating hair loss, filling wrinkles or contouring the face or body of a subject. The cosmetic, nonmedical, use does not involve treatment of any form of disease or medical condition. Examples of improving the appearance of the skin include, but are not limited to, treatment of sun-damaged or aged skin, skin revitalization, skin whitening and treatment of hyper pigmentation disorders such as senile freckles, melisma, and nephelines.

Definitions

While the following terms are believed to be well understood by one of ordinary skill in the art, the following definitions are set forth to facilitate explanation of the presently disclosed subject matter.

The term "a" or "an" may refer to one or more of that entity, i.e. can refer to plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, the terms "about" or "approximately" when preceding a numerical value indicates the value plus or minus a range of 10% of the value.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, a "control" is an alternative sample used in an experiment for comparison purpose. A control can be "positive" or "negative." A "control sample" or "reference sample" as used herein, refers to a sample or reference that acts as a control for comparison to an experimental sample. For example, an experimental sample comprises compound A, B, and C in a vial, and the control may be the same type of sample treated identically to the experimental sample, but lacking one or more of compounds A, B, or C.

As used herein, the term "effective amount" refers to a quantity sufficient to achieve a desired therapeutic and/or prophylactic effect, e.g., an amount which results in the prevention of one or more outcomes, or an increase in one more outcomes.

As used herein, the terms "individual", "patient", or "subject" can be an individual organism, a vertebrate, a mammal, or a human. In a preferred aspect, the individual, patient, or subject is a human.

As used herein, the phrase "soft tissue" refers to tissues that connect, support, or surround other structures and organs of the body. Soft tissue includes muscles, fibrous tissues, and fat.

As used herein, the phrase "soft tissue augmentation" refers to any type of volume augmentation of soft tissues, including, but not limited to facial contouring (e.g., more pronounced cheeks, chin, or lips), correction of concave deformities (e.g., post-traumatic or HIV-associated lipoatrophy), and correction of deep age-related facial folds. Thus, soft tissue augmentation may be used for cosmetic purposes or for medical purposes, such as those following trauma or degenerative disease. Soft tissue augmentation further refers to dermal filling, body contouring, and gingival filling.

As used herein, the phrase "non-animal origin" refers to a source that excludes animals, but includes sources such as yeast, bacteria, or synthetic.

As used herein, the term "bioresorbable" refers to a degradation event or events-bioresorbable substances may dissolve, may be phagocytized, or may simply degrade over a period of time such that the substances are cleared from the body, organ, tissue, location, or cell over a period of time. The substances or degradation products thereof may be metabolized, incorporated into other molecules or compounds, or excreted.

As used herein, the term "aseptic" refers to something that is free or freed from pathogenic microorganisms.

As used herein, the term "sterile" refers to something that is free of living organisms, generally free of living microorganisms.

As used herein, the term "injectable" refers to the ability to inject a composition of the present disclosure through a needle.

As used herein, the terms "MW" or "Mw" refer to the mass average molecular mass.

As used herein, the term "$Mw_{app}$" refers to apparent MW, which is a simulated value for the molecular weight of GAGs in hydrogels.

As used herein, the term "SwF" refers to the swelling factor analysis in 0.9% saline, which is the volume of 1 gram gel that has swelled to its maximum in 0.9% saline—usually represented in mL/g.

As used herein, "gel part" or "GelP" refer to the percentage in the proportion of the total HA that is bound in gel form—further described as the amount of HA in a sample that does not pass through a 0.22 micrometer filter. The GelC is calculated from the amount of HA that is collected in the filtrate and is reported as the percentage of the total amount of HA in the gel sample. GelP is generally a description of the percentage of PS that is a part of the gel network. A number of 90% means that 10% of the polysaccharide is not a part of the gel network.

Mw—The mass average molecular mass

SwD—SwellingDegree. SwD is preferably expressed in g/g, mL/g, or as a dimensionless number. SwD is the inverted concentration of gel-form GAG in a gel that is fully swollen in 0.9% saline, i.e. the volume, or mass, of fully swollen gel that can be formed per gram dry cross-linked GAG. SwD describes the maximum liquid-absorbing (0.9% saline) capability of the product.

$$SwD = \frac{m_{fully\ swollen\ gel}}{m_{gel-form\ GAG\ in\ fully\ swollen\ gel}}$$

The SwD may also be expressed as:

$$SwD = \frac{Swf}{m_{final} * GelP}$$

$C_{min}$—Minimum theoretical GAG concentration, Concentration of gel-form GAG in a gel that is fully swollen in 0.9% saline, normally expressed in mg/g or mg/mL.

$$C_{min}^{-1} = SwD$$

$C_{final}$—The intended GAG concentration for a hydrogel product. Concentration of gel-form GAG in a gel product that is swollen in 0.9% saline, normally expressed in mg/g or mg/mL.

$CrR_{DATH}$—Effective crosslinking ratio was analyzed with LC-SEC-MS and defined as:

$$CrR = \frac{\text{mol crosslinked crosslinker with amide bonds}}{\text{mol linked crosslinker with amide bonds}}$$

A CrR of 1.0 means that all of the crosslinker has crosslinked. A CrD ($CrD_{amide}$) of 1 means that all of the HA disaccharides are crosslinked.

In some aspects the composition is bioresorbable. In some aspects, the hydrogel is bioresorbable. In some aspects, the composition is bioresorbed within a period of about 1 year to about 3 years. In some aspects, the composition is bioresorbed within a period of 1 year to 3 years. In some aspects, the hydrogel is bioresorbed within a period of about 1 year to about 3 years. In some aspects, the hydrogel is bioresorbed within a period of 1 year to 3 years.

In some aspects, the composition further comprises a local anesthetic. In some aspects, the composition comprises at least one local anesthetic. In some aspects the local anesthetic is an amide-type local anesthetic. In some aspects, the local anesthetic is an ester-type local anesthetic In some aspects, the local anesthetic is selected from the group consisting of: bupivacaine, butanilicaine, carticaine, cinchocaine (dibucaine), clibucaine, ethyl parapiperidinoacetylaminobenzoate, etidocaine, lignocaine (lidocaine), mepivacaine, oxethazaine, prilocaine, ropivacaine, tolycaine, trimecaine, vadocaine, articaine, levobupivacaine, amylocaine, cocaine, propanocaine, clormecaine, cyclomethycaine, proxymetacaine, amethocaine (tetracaine), benzocaine, butacaine, butoxycaine, butyl aminobenzoate, chloroprocaine, dimethocaine (larocaine), oxybuprocaine, piperocaine, parethoxycaine, procaine (novocaine), propoxycaine, and tricaine; or a combination thereof.

In some aspects, the concentration of local anesthetic in the composition is between 1 to 5 mg/mL. In some aspects, the concentration of local anesthetic in the composition is between about 1 to about 5 mg/mL. In some aspects, the concentration of local anesthetic in the composition is between 2 to 4 mg/mL. In some aspects, the concentration of local anesthetic in the composition is between about 2 to about 4 mg/mL. In some aspects, the concentration of local anesthetic in the composition is 0.5 mg/mL, 1 mg/mL, 1.5 mg/mL, 2 mg/mL, 2.5 mg/mL, 3 mg/mL, 3.5 mg/mL, 4 mg/mL, 4.5 mg/mL, or 5 mg/mL. In some aspects, the concentration of local anesthetic in the composition is about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, or about 5 mg/mL.

In some aspects, the composition is injectable. In some aspects, the injectable composition is an injectable implant. In some aspects, the disclosure is drawn to an injectable implant comprising any one of the compositions disclosed herein. In some aspects, the injectable implant is for subdermal, intradermal, subcutaneous, intramuscular, submuscular, intragingival injection.

In some aspects, the disclosure is drawn to a pre-filled syringe comprising any one of the compositions disclosed herein. In some aspects, the disclosure is drawn to a pre-filled vial comprising any one of the compositions disclosed herein.

In some aspects, a kit comprises a pre-filled syringe comprising any one of the compositions disclosed herein. In some aspects, a kit comprises a pre-filled vial comprising any one of the compositions disclosed herein, a syringe, and one or more hypodermic needles. In some cases the kit comprises an antimicrobial composition for administering to the site of injection.

In some aspects, kits for use in practicing the methods described herein are contemplated. In some aspects, kits comprise all solutions, buffers, compounds, vessels, and/or instructions sufficient for performing the methods described herein.

In some aspects, the composition further comprises sodium chloride. In some aspects, the composition exhibits a sodium chloride concentration of 0.9% w/v. In some aspects, the composition exhibits a sodium chloride concentration of 0.7% when lidocaine is present in the composition. In some aspects, the compositions exhibits a sodium chloride concentration of 0.9% when lidocaine is absent from the composition. In some aspects, the composition further comprises a phosphate buffer. In some aspects, the composition further comprises a pharmaceutically acceptable carrier. In some aspects the composition further comprises sodium chloride, a phosphate buffer, and a pharmaceutically acceptable carrier. In some aspects, the phosphate buffer is PBS.

In some aspects, the composition comprises one or more density enhancing agents. In some aspects, the density enhancing agents may be selected from sorbitol, mannitol, and fructose.

In some aspects, the composition comprises a buffering agent. A buffering agent is a chemical compound that is or compounds that are added to a solution to allow that solution to resist changes in pH as a result of either dilution or small additions of acids or bases. Effective buffer systems employ solutions which contain large and approximately equal concentrations of a conjugate acid-base pair (or buffering agents). A buffering agent employed herein may be any such chemical compound(s) which is pharmaceutically acceptable, including but not limited to salts (conjugates acids and/or bases) of phosphates and citrates. In some aspects, the buffering agent comprises phosphate buffered saline (PBS) or an alternative phosphate buffer.

In some aspects, the composition is aseptic. In some aspects, the composition is sterile. In some aspects, the composition is sterilized via filtration sterilization, heat sterilization, or irradiation sterilization. In some aspects, components of the composition are sterilized prior to mixing or forming the whole composition, thus resulting in a composition that comprises two or more components that were sterilized prior to forming the composition.

Methods of Using the Hydrogels

In some aspects, the present disclosure comprises methods of performing reparative or esthetic dermatologic treatment. In some aspects, the reparative or esthetic dermatologic treatment comprises injecting a subject with a composition disclosed herein. In some aspects, the injection is a subdermal, intradermal, subcutaneous, intramuscular, submuscular, or intragingival injection.

In some aspects, methods of the present disclosure are drawn to intragingival injection to fill the gums as a result of receding gums. In some aspects, methods are drawn to injection of the composition in one or more tissues of the oral cavity.

In some aspects, the injection is for dermal filling, body contouring, facial contouring, and gingival filling.

In some aspects, the injection of a composition disclosed herein is for dermal filling. In some aspects, methods of dermal filling include injection of the composition to fill skin cracks. In some aspects, methods of dermal filling include injection of the composition to fill fine lines in the face, neck, hands, feet, knees, and elbows. In some aspects, methods of dermal filling include injection of the composition to fill fine wrinkles in the face, neck, hands, feet, knees, and elbows. In some aspects, methods of dermal filling include injection of the composition to fill fine lines in the face, neck, hands, feet, knees, and elbows.

In some aspects, methods of dermal filling include injection of the composition to fill scars. In some aspects, methods of dermal filling include injection of the composition to fill depressed scars. In some aspects, methods of dermal filling include injection of the composition to fill hypertrophic scars. In some aspects, methods of dermal filling include injection of the composition to fill keloid scars.

In some aspects, methods of dermal filling include injection of the composition to restore and/or correct for signs of facial fat loss (lipoatrophy) in people with human immunodeficiency virus (HIV).

In some aspects, methods of dermal filling include injection of the composition to the backs of hands or the top of feet.

In some aspects, methods of dermal filling include injection of the composition to strengthen weakened vocal cords.

In some aspects, methods of dermal filling include injection of the composition to restore lost volume to a portion of the body as a result of age, illness, or injury.

In some aspects, methods of facial contouring include injection of the composition to the face to modify the facial contour. In some aspects, methods of facial contouring include injection of the composition to the lips to augment the size and/or shape of the lips.

In some aspects, methods of facial contouring include injection of the composition to the face to increase facial symmetry. In some aspects, methods of facial contouring include injection of the composition to change the shape of the face to an oval shape, round shape, square shape, triangle shape, inverted triangle shape, rectangular shape, or oblong shape. In some aspects, methods of facial contouring include injection of the composition to increase the total width of the face. In some aspects, methods of facial contouring include injection of the composition to increase the total length of the face.

In some aspects, methods of facial contouring include injection of the composition to the face to increase the forehead and/or cheekbone width. In some aspects, methods of facial contouring include injection of the composition to the face to increase the length of the jawline.

In some aspects, methods of facial contouring include injection of the composition to the face to change the size and/or shape of the chin. In some aspects, methods of facial contouring include injection of the composition to the face to change the size and/or shape of the forehead. In some aspects, methods of facial contouring include injection of the composition to the face to change the size and/or shape of the cheeks. In some aspects, methods of facial contouring include injection of the composition to the face to change the size and/or shape of the brow.

In some aspects, methods of facial contouring include injection of the composition to the face to modify the appearance associated with retrognathia. In some aspects, methods of facial contouring include injection of the composition to the face to modify the appearance associated with prognathism.

In some aspects, methods of body contouring include injection of the composition to the body to modify the size and shape of various aspects of the body. In some aspects, methods of body contouring include injection of the composition to the body to modify the size and shape of aspects of the body to increase symmetry.

In some aspects, methods of body contouring include injection of the composition to the body to modify the size and shape of the breasts, buttocks, sacrum, groin, hips, abdomen, thorax, feet, legs, knees, popliteus, thighs, arms, hands, elbows, and/or antecubitis.

In some aspects, methods of body contouring include injection of the composition to the body to fill a concave deformity. In some aspects, the concave deformity is a result of age, illness, injury, or predisposition. In some aspects, methods of body contouring include injection of the composition to the body to decrease the appearance of cellulite.

The present technology is not to be limited in terms of the particular aspects described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

EXAMPLES

Without desiring to be limited thereto, the present disclosure will in the following be illustrated by way of the following experimental examples. Hyaluronic acid was used in the schematic crosslinking and post-crosslinking procedure outlined in FIG. 1.

Example 1—Crosslinking of HMW HA and Post-Crosslinking Alkaline Degradation

Two stock solutions, DMTMM and the crosslinker (DATH), were freshly prepared in 8 mM phosphate buffer. A reaction solution was prepared by adding desired volumes of the DMTMM (mol % DATH×10) and DATH (see Table 1) stock solutions, respectively, to 8 mM phosphate. The reaction solution was mixed and directly added to pre-weighted HA (1000 kDa) in a reaction vessel. The mixture was extensively mixed for 3 min and incubated. After 24±2 h, the obtained material was pressed through a 1 mm steel mesh twice followed by addition of NaOH (Table 1).

The material was left to degrade for 24±2 h in ambient temperature before the solution was neutralized using HCl and subsequently precipitated by adding EtOH. The obtained powder was dried under vacuum overnight and reconstituted in 1 mM PBS. The gel was subjected to particle size reduction (PSR) using 3×125 μm filter, filled in syringes and subsequently sterilized ($F_0 23$).

TABLE 1

Reaction conditions and obtained gel properties.

| | Reaction Conditions | | | Gel Properties | | | | |
|---|---|---|---|---|---|---|---|---|
| Exp | DATH/HA (mol %) | [HA] (%) | NaOH (M) | SwF (mL/g) | $C_{final}$ (mg/mL) | GelP (%) | G' (Pa) | $C_{min}$ (mg/mL) |
| 1-1 | 0.26 | 15 | 0.5 | 5.7 | ND | 46 | ND | ND |
| 1-2 | 0.26 | 15 | 1.0 | ND | ND | 37 | ND | ND |
| 1-3 | 0.54 | 15 | 1.0 | 2.5 | 17.2 | 89 | 244 | 6.1 |
| 1-4 | 0.43 | 15 | 1.0 | 3.2 | 16.8 | 70 | ND | 3.7 |
| 1-5 | 0.43 | 15 | 1.5 | 5.1 | 17.1 | 52 | ND | 1.7 |
| 1-6 | 0.49 | 15 | 1.5 | 3.7 | 16.7 | 64 | ND | 2.9 |
| 1-7 | 0.49 | 15 | 2.0 | 4.6 | 16.9 | 37 | ND | 1.4 |
| 1-8 | 0.67 | 15 | 1.5 | 3.2 | 20.0 | 73 | ND | 4.6 |
| 1-9 | 0.67 | 15 | 2.0 | 3.7 | 19.8 | 59 | ND | 3.2 |
| 1-10 | 0.83 | 15 | 1.5 | 2.3 | 20.2 | 80 | ND | 7.0 |
| 1-11 | 0.83 | 15 | 2.0 | 2.9 | 20.0 | 66 | ND | 4.6 |
| 1-12 | 0.50 | 10 | 1.0 | 6.5 | 18.9 | 64 | 32 | 1.9 |
| 1-13 | 0.50 | 12.5 | 1.0 | 5.0 | 19.4 | 67 | 35 | 2.6 |
| 1-14 | 0.60 | 10.0 | 1.0 | 5.9 | 19.3 | 66 | ND | 2.2 |
| 1-15 | 0.60 | 12.5 | 1.0 | 4.3 | 19.1 | 79 | ND | 3.5 |

ND = Not determined

Thus, through the use of a post-crosslinking degradation step, it was possible to obtain different gel properties when starting from HMW hyaluronic acid (1000 kDa).

Example 2-1—Crosslinking of HA (400 kDa) Using a Non-Degrading Process

Two stock solutions, DMTMM and the crosslinker (DATH), were freshly prepared in 8 mM phosphate buffer. One reaction solution was prepared by adding DMTMM (6.8 mol %/HA) and DATH (0.8 mol %/HA), respectively, to 8 mM phosphate buffer.

The reaction solution was mixed and directly added to pre-weighted HA (400 kDa) in a reaction vessel. The mixture was extensively mixed for 3.5 min and incubated.

After 24 h, the obtained material was pressed through a 1 mm steel mesh twice followed by addition of 0.25 M NaOH. The material was stirred for 1 h in ambient temperature before the mixture was neutralized using HCl and subsequently precipitated by adding EtOH. The obtained powder was dried in under vacuum overnight and reconstituted in 8 mM phosphate with 0.9% NaCl. The gel was subjected to particle size reduction (PSR) using 3×315 μm filter, filled in syringes and subsequently sterilized ($F_0 23$). The reaction sequence gives a crosslinked hydrogel, reaction conditions and obtained gel properties are presented in Table 2.

Example 2-2—Determination of Mw for Crosslinking Using a Non-Degrading Process One stock solution with DMTMM was freshly prepared in 8 mM phosphate buffer. One reaction solution was prepared by adding DMTMM (6.8 mol %/HA) to 8 mM phosphate buffer. The reaction solution was directly added to pre-weighted HA (400 kDa) in a reaction vessel. The mixture was extensively mixed for 3.5 min and incubated. After 24 h, the obtained material was diluted with 0.25 M NaOH. The material was stirred for 1 h in ambient temperature before the mixture was neutralized using HCl and subsequently precipitated by adding EtOH. The obtained powder was dried in under vacuum overnight and reconstituted in 8 mM phosphate with 0.9% NaCl. The solution was subjected to particle size reduction (PSR) using 3×315 μm filter, filled in syringes and subsequently sterilized ($F_0 23$).

Example 3-1—Crosslinking of HA (400 kDa) Using a Non-Degrading Process

Two stock solutions, DMTMM and the crosslinker (DATH), were freshly prepared in 8 mM phosphate buffer. One reaction solution was prepared by adding DMTMM (6.0 mol %/HA) and DATH (0.6 mol %/HA), respectively, to 8 mM phosphate buffer.

The reaction solution was mixed and directly added to pre-weighted HA (400 kDa) in a reaction vessel. The mixture was extensively mixed for 3.5 min and incubated.

After 24 h, the obtained material was pressed through a 1 mm steel mesh twice followed by addition of 0.25 M NaOH. The material was stirred for 1 h in ambient temperature before the mixture was neutralized using HCl and subsequently precipitated by adding EtOH. The obtained powder was dried in under vacuum overnight and reconstituted in 8 mM phosphate with 0.9% NaCl. The gel was subjected to particle size reduction (PSR) using 3×315 μm filter, filled in syringes and subsequently sterilized ($F_0 23$). The reaction sequence gives a crosslinked hydrogel, reaction conditions and obtained gel properties are presented in Table 3.

Example 3-2—Crosslinking of HA (1 000 kDa) and Post-Crosslinking Alkaline Degradation Two stock solutions, DMTMM and the crosslinker (DATH), were freshly prepared in 8 mM phosphate buffer. One reaction solution was prepared by adding DMTMM (6.0 mol %/HA) and DATH (0.6 mol %/HA), respectively, to 8 mM phosphate buffer.

The reaction solution was mixed and directly added to pre-weighted HA (1000 kDa) in a reaction vessel. The mixture was extensively mixed for 3.5 min and incubated. After 24 h, the obtained material was pressed through a 1 mm steel mesh twice followed by addition of 1.0 M NaOH. The material was stirred for 24 h in ambient temperature before the mixture was neutralized using HCl and subsequently precipitated by adding EtOH. The obtained powder was dried in under vacuum overnight and reconstituted in 8 mM phosphate with 0.9% NaCl. The gel was subjected to particle size reduction (PSR) using 3×315 μm filter, filled in syringes and subsequently sterilized ($F_0 23$). The reaction sequence gives a crosslinked hydrogel, reaction conditions and obtained gel properties are presented in Table 3.

TABLE 2

Reaction conditions and Mw for the obtained solutions.

| | Reaction Conditions | | | | | Gel Properties | | | | End |
|---|---|---|---|---|---|---|---|---|---|---|
| Exp. | DATH/HA (mol %) | DMTMM/ HA | Start <Mw> | [HA] (%) | NaOH | SwF (mL/g) | $C_{final}$ (mg/mL) | GelP (%) | $C_{min}$ (mg/mL) | <Mw> (kDa) |
| 2-1 | 0.80 | 6.8 | 400 | 5 | 0.25M/ 1 h | 8.0 | 26.2 | 7.4 | 2.4 | NA |
| 2-2 | 0.00 | 6.8 | 400 | 5 | 0.25M/ 1 h | NA | NA | NA | NA | 380 |

NA = Not Applicable

For Exp 2-1 and 2-2, HA (Mw 400 kDa) was subjected to similar processes but excluding the diaminocrosslinker in Exp 2.2. The process used in Exp 2-1 and Exp 2-2 gives minor degradation (decrease of Mw for 2-2:400 to 380 kDa) of the polysaccharide showing that 0.25 M NaOH for 1 h process is not sufficient to be considered as degrading.

Example 3-3—Determination of Mw for Crosslinking of HA (1 000 kDa) and Post-Crosslinking Alkaline Degradation One stock solution with DMTMM was freshly prepared in 8 mM phosphate buffer. One reaction solution was prepared by adding DMTMM (6.0 mol %/HA) to 8 mM phosphate buffer. The reaction solution was directly added to pre-weighted HA (1 000 kDa) in a reaction vessel. The mixture was extensively mixed for 3.5 min and incubated. After 24 h, the obtained material was diluted with 1.0 M NaOH. The material was stirred for 24 h in ambient temperature before the mixture was neutralized using HCl and subsequently precipitated by adding EtOH. The obtained powder was dried in under vacuum overnight and reconstituted in 8 mM phosphate with 0.9% NaCl. The solution was subjected to particle size reduction (PSR) using 3×315 μm filter, filled in syringes and subsequently sterilized ($F_0 23$).

Thus, with the same starting material, it was possible to obtain various gel properties trough the post-crosslinking degradation step. Using this specific step, a gel having lower elastic modulus G' could be obtained, i.e. the gels from 4-1 and 4-2 had a lower G' than the gel of 4-3. After the post-crosslinking degradation step, gels from Exp 4-1 & 4-2 can be formulated to $C_{final}$ 25 mg/mL, which is not valid for Exp 4-3 due to the higher $C_{min}$ in Exp 4-3.

TABLE 3

Reaction conditions and Mw for the obtained solutions.

| | Reaction Conditions | | | | Start | | Gel properties | | | End |
|---|---|---|---|---|---|---|---|---|---|---|
| Exp | DMTMM/ DATH/HA (mol %) | HA (mol %) | <Mw> (kDa) | [HA] (%) | NaOH | SwF (mL/g) | $C_{final}$ (mg/mL) | GelP (%) | $C_{min}$ (mg/mL) | <Mw> (kDa) |
| 3-1 | 0.60 | 6.0 | 400 | 12.5 | 0.25M/1 h | 1.9 | 24.3 | 88 | 11.3 | NA |
| 3-2 | 0.60 | 6.0 | 1000 | 12.5 | 1.0M/24 h | 3.3 | 27.3 | 74 | 6.1 | NA |
| 3-3 | 0.0 | 6.0 | 1000 | 12.5 | 1.0M/24 h | NA | NA | NA | NA | 540 |

NA = Not Applicable

Exp 3-1 and 3-2, show that hydrogels can be manufactured starting from HA 400 kDa (exp 3-1) or from HA 1 000 kDa (exp 3-2) but including a post-crosslinking alkaline treatment (1.0 M NaOH for 24 h). Suitable hydrogels for dermal injections can be produced from HA 1000 kDa. Exp 3-3 shows the estimated apparent Mw ($Mw_{app}$) decrease in the process used for exp 3-2 starting from HA 1000 kDa, this verify the apparent Mw in the gel network for exp 3-1 and exp 3-2 to be similar.

Example 4—Crosslinking of HMW HA and Post-Crosslinking Degradation

Two stock solutions, DMTMM and the crosslinker (DATH), were freshly prepared in water. Desired volumes of the stock solutions, DMTMM (7.5 mol %) and DATH (0.75 mol %) respectively, were added to pre-weighted HA (760 kDa) in a reaction vessel to yield a final concentration of HA to 15% in the reaction mixture. The mixture was extensively mixed for 3.5 min and subsequently incubated. After 24 h at ambient temperature, the obtained material was pressed through a 1 mm steel mesh twice.

After pressing through steel mesh, the bulk material was split in 3 different sub-batches (Exp 4-1 to 4-3). Sub-batch 4-1 and 4-2 was subjected to hydrolysis for 24±2 h in ambient temperature according to Table 4 before the reaction was neutralized to approx. pH 7 using HCl. The control reaction (4-3) was stirred in water for 24 h at ambient temperature. The three sub-batches were subsequently precipitated by adding EtOH. The obtained powder was dried in under vacuum overnight and reconstituted in 1 mM phosphate with 0.9% NaCl. Reaction conditions and obtained gel properties are presented in Table 4.

TABLE 4

Reaction conditions and obtained gel properties.

| | | Gel properties | | | | | |
|---|---|---|---|---|---|---|---|
| Exp | Degradation Conditions | SwF (mL/g) | $C_{final}$ (mg/mL) | GelP (%) | $C_{min}$ (mg/mL) | G' (Pa) | CrR |
| 4-1 | NaOH (1.0M) | 5.3 | 71 | 89 | 11.8 | 3329 | 0.92 |
| 4-2 | NaOH (2.0M) | 7.7 | 70 | 77 | 7.0 | 1279 | 0.85 |
| 4-3 | No degradation | 2.0 | 74 | 100 | 37.2 | 5261 | 0.88 |

Example 5—Determination of the Apparent Mw ($Mw_{app}$) for Hydrogels Using a Degrading Process One stock solution of DMTMM was freshly prepared in water. Desired volume of the stock solution, DMTMM (7.5 mol %), was added to pre-weighted HA (760 kDa) in a reaction vessel to yield a final concentration of HA to 15% in the reaction mixture. The mixture was extensively mixed for 3.5 min and subsequently incubated at ambient temperature. After 24 h, the obtained material was subjected to conditions according to Table 5 before the mixture was neutralized to approx. pH 7 using HCl and diluted in saline to HA conc. of approx. 5 mg/ml.

TABLE 5

Degradation conditions and Mw for the obtained solutions.

| Exp | Degradation Conditions | <Mw> (kDa) |
|---|---|---|
| 5-1 | NaOH (1.0M) | 410 |
| 5-2 | NaOH (2.0M) | 380 |
| 5-3 | No degradation | 760 |

Example 5 shows that the post-crosslinking degradation step reduces the apparent Mw as compared to a gel which has not been subjected to degradation.

Example 6—Crosslinking of HMW HA and Post-Crosslinking Degradation

Two stock solutions, DMTMM and the crosslinker (DATH), were freshly prepared in water. Desired volumes of the stock solutions of DMTMM and DATH were mixed before addition to pre-weighted HA (990 kDa) in 2 reaction vessels. The reaction mixtures, with compositions according to Table 6, were extensively mixed for 3.5 min and subsequently incubated. After 24 h at ambient temperature, the obtained material was pressed through a 1 mm steel mesh twice. After pressing through steel mesh, the bulk material from each vessel was split in 2 different sub-batches (Exp 6-1-6-2 and Exp 6-3-6-4). Sub-batch 6-2 and 6-4 were subjected to hydrolysis at 1.0 M NaOH for 24 h at ambient temperature according to Table 6 before the reaction was neutralized to approx. pH 7 using HCl. The control reactions (6-1 and 6-3) were subjected to the same treatment but in water instead of NaOH. The neutralized bulks were precipitated by adding EtOH. The obtained powder was dried in under vacuum overnight and reconstituted in 1 mM phosphate with 0.9% NaCl.

TABLE 6

Reaction conditions and obtained gel properties.

| | Reaction Conditions | | | | | Gel properties | | | | |
|---|---|---|---|---|---|---|---|---|---|---|
| Exp | DATH/HA (mol %) | DMTMM/HA (mol %) | Start <Mw> (kDa) | [HA] (%) | NaOH | $C_{final}$ (mg/mL) | GelP (%) | SwF (mL/g) | $C_{min}$ (mg/mL) | CrR |
| 6-1 | 0.59 | 5.0 | 990 | 17.5 | water/24 h | 100 | 100 | 2.2 | 45 | 0.87 |
| 6-2 | 0.59 | 5.0 | 990 | 17.5 | 1.0M/24 h | 20 | 33 | 3.4 | 2 | 0.88 |
| 6-3 | 0.90 | 7.7 | 990 | 12.5 | water/24 h | 99 | 100 | 2.9 | 34 | 0.86 |
| 6-4 | 0.90 | 7.7 | 990 | 12.5 | 1.0M/24 h | 20 | 58 | 3.9 | 3 | 0.88 |

Thus, with the same starting material, it was possible to obtain different gel properties trough the post-crosslinking degradation step. Using this specific step, a gel having a decreased $C_{min}$ could be obtained, i.e. the gels of 6-2 and 6-4 had a lower $C_{min}$ than the gels of 6-1 and 6-3 respectively. Through this specific step, it is possible to obtain gels that can be reconstituted to a final HA-concentration ($C_{final}$) of 20 mg/mL without phase-separation ($C_{min} \leq C_{final}/2$). The crosslinking ratio (CrR) is not effected by the post-crosslinking degradation, indicating that the decreased $C_{min}$ originates from degradation of the hyaluronan backbone (as shown by Mw in example 7) rather the hydrolysis of the crosslinker.

Example 7—Determination of the Apparent MW ($MW_{app}$) for Hydrogels Using a Degrading Process One stock solution of DMTMM was freshly prepared in water. Desired volumes of the stock solution DMTMM was added to pre-weighted HA (990 kDa) in 2 reaction vessels. The reaction mixtures, with compositions according to Table 7, were extensively mixed for 3.5 min and subsequently incubated at ambient temperature. After 24 h at ambient temperature, the obtained material was pressed through a 1 mm steel mesh twice. After pressing through steel mesh, the bulk material from each vessel was split in 2 different sub-batches (Exp 7-1-7-2 and Exp 7-3-7-4). Sub-batch 7-2 and 7-4 were subjected to hydrolysis at ambient temperature in 1.0 M NaOH for 24 h. The control batches 7-1 and 7-3 were swelled in water for 24 h at ambient temperature and subsequently subjected to 0.4 M NaOH at ambient temperature for 0.5 h before the reaction was neutralized to approx. pH 7 using HCl.

TABLE 7

Reaction conditions and obtained $MW_{app}$.

| | Reaction Conditions | | | | | Apparent Mw | | |
|---|---|---|---|---|---|---|---|---|
| Exp | DATH/HA (mol %) | DMTMM/HA (mol %) | Start <Mw> (kDa) | [HA] (%) | NaOH | <Mw> (kDa) | <Mn> (kDa) | Pd |
| 7-1 | 0 | 5.0 | 990 | 17.5 | water/24 h | 910 | 0.60 | 1.5 |
| 7-2 | 0 | 5.0 | 990 | 17.5 | 1.0M/24 h | 260 | 0.17 | 1.6 |
| 7-3 | 0 | 7.7 | 990 | 12.5 | water/24 h | 950 | 0.65 | 1.5 |
| 7-4 | 0 | 7.7 | 990 | 12.5 | 1.0M/24 h | 270 | 0.17 | 1.6 |

Exp 7-2 and 7-4 demonstrated that the post-crosslinking degradation step reduces the apparent Mw as compared to a gel which has not been subjected to degradation, Exp 7-1 and 7-3.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the disclosure claimed. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein. The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

In addition, where features or aspects of the disclosure are described in terms of Markush groups, those skilled in the art will recognize that the disclosure is also thereby described in terms of any individual member or subgroup of members of the Markush group.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

The invention claimed is:

1. A method of preparing a hydrogel product comprising crosslinked glycosaminoglycan molecules at a concentration $C_{final}$ (mg/mL), the method comprising:
   (a) crosslinking a glycosaminoglycan having a molecular weight of above 700 kDa in conditions so as to provide a glycosaminoglycan hydrogel crosslinked by amide bonds and having a $C_{min}$ (mg/mL) that is above $C_{final}/2$, wherein $C_{min}$ is the concentration of gel-form glycosaminoglycan in the gel when fully swollen in physiological buffer;
   (b) subjecting the hydrogel from (a) to post-crosslinking degradation of the glycosaminoglycan backbone in 1.0 M to 3.0 M NaOH for 24-48 hours, thereby reducing the $C_{min}$ of the hydrogel to a value that is below $C_{final}/2$, wherein the post-crosslinking degradation decreases the apparent molecular weight ($Mw_{app}$) of the glycosaminoglycan backbone by 15% to 90%; and
   (c) formulating the partially degraded hydrogel obtained from (b) to form an injectable hydrogel composition having a concentration of glycosaminoglycan molecules of $C_{final}$ (mg/mL).

2. The method according to claim 1, wherein the $C_{min}$ of the hydrogel is reduced to below 15 mg/mL.

3. The method according to claim 1, wherein the $C_{min}$ of the hydrogel is reduced to 0.5-15 mg/mL in (b).

4. The method according to claim 1, wherein $C_{final}$ is above 10 mg/mL.

5. The method according to claim 1, wherein $C_{final}$ is between 10-30 mg/mL.

6. The method according to claim 1, wherein the crosslinking of (a) is performed at a GAG concentration of above 60 mg/mL.

7. The method according to claim 1, wherein the post-crosslinking degradation of (b) decreases the apparent molecular weight ($Mw_{app}$) of the crosslinked glycosaminoglycan with at least 25%.

8. The method according to claim 1, wherein the hydrogel in (a) is crosslinked to an extent such that it is phase-separated when diluted to 20 mg/ml at pH 6.0-8.0 in 1.0 mM-20 mM phosphate buffer and wherein the post-crosslinking degradation of (b) is to an extent such that the hydrogel is not phase-separated when diluted to 20 mg/ml at pH 6.0-8.0 in 1.0 mM-20 mM phosphate buffer.

9. The method according to claim 1, wherein the crosslinking of (a) is performed at a pH of 5.0-9.0.

10. The method according to claim 1, wherein the crosslinking of (a) is performed at a pH of 6.0-8.0.

11. The method according to claim 1, wherein the crosslinking (a), comprises:
    (i) providing a solution of glycosaminoglycan molecules;
    (ii) activating carboxyl groups on the glycosaminoglycan molecules with a coupling agent to form activated glycosaminoglycan molecules; and
    (iii) crosslinking the activated glycosaminoglycan molecules via their activated carboxyl groups using a di- or multinucleophile functional crosslinker comprising a spacer group selected from the group consisting of di-, tri-, tetra-, and oligosaccharides to obtain crosslinked glycosaminoglycan molecules.

12. The method according to claim 11, wherein the crosslinker is diaminotrehalose (DATH).

13. The method according to claim 11, wherein the post-crosslinking degradation comprises reducing the effective crosslinking ratio (CrR) of the glycosaminoglycan less than 10%.

14. The method according to claim 1, wherein the crosslinking comprises crosslinking an at least partially N-deacetylated glycosaminoglycan by amide bonds between carboxyl groups and free amine groups on the glycosaminoglycan backbone to provide the glycosaminoglycan hydrogel crosslinked by amide bonds.

15. The method according to claim 14, wherein the post-crosslinking degradation comprises reducing the effective crosslinking degree (CrD) of the glycosaminoglycan less than 10%.

16. The method according to claim 1, wherein the glycosaminoglycan is hyaluronic acid.

17. The method according to claim 1, wherein the post-crosslinking degradation decreases the apparent molecular weight ($Mw_{app}$) of the glycosaminoglycan backbone by 25% to 80%.

* * * * *